US009078706B2

(12) United States Patent
Kirschman

(10) Patent No.: US 9,078,706 B2
(45) Date of Patent: *Jul. 14, 2015

(54) INTERVERTEBRAL FUSION DEVICE UTILIZING MULTIPLE MOBILE UNIAXIAL AND BIDIRECTIONAL SCREW INTERFACE PLATES

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 570 days.

This patent is subject to a terminal disclaimer.

(21) Appl. No.: 13/409,377

(22) Filed: Mar. 1, 2012

(65) Prior Publication Data

US 2012/0197399 A1 Aug. 2, 2012

Related U.S. Application Data

(60) Continuation-in-part of application No. 12/640,061, filed on Dec. 17, 2009, now Pat. No. 8,282,682, which is a continuation-in-part of application No. 11/624,341, filed on Jan. 18, 2007, now Pat. No.

(Continued)

(51) Int. Cl.
*A61F 2/44* (2006.01)
*A61B 17/70* (2006.01)
(Continued)

(52) U.S. Cl.
CPC ......... *A61B 17/7059* (2013.01); *A61B 17/8042* (2013.01); *A61B 17/8047* (2013.01);
(Continued)

(58) Field of Classification Search
CPC ........... A61B 17/7059; A61B 17/8047; A61B 17/8057; A61B 17/8605; A61B 17/8042; A61B 39/101; A61F 2/44; A61F 2/4465; A61F 2/447; A61F 2002/4629; A61F 2/30744; A61F 2002/2835; A61F 2002/30062; A61F 2002/30131; A61F 2002/30383; A61F 2002/30385; A61F 2002/30398; A61F 2002/305; A61F 2002/30505; A61F 2002/30507; A61F 2002/30517; A61F 2002/30576; A61F 2002/30578; A61F 2002/30604; A61F 2002/30616; A61F 2002/30784; A61F 2002/30785; A61F 2002/30794; A61F 2002/30904; A61F 2002/4475; A61F 2002/449; A61F 2310/00017; A61F 2310/00023; A61F 2310/00161; A61F 2002/30189; A61F 2002/30387; A61F 2002/30774; A61F 2002/30787; F16B 41/002
USPC .................... 623/17.11–17.16; 606/246–295
See application file for complete search history.

(56) References Cited

U.S. PATENT DOCUMENTS 1,025,008 A 4/1912 Miner
1,037,577 A 9/1912 Baker
(Continued)

FOREIGN PATENT DOCUMENTS

CA 1292596 C 12/1991
CA 2133276 C 4/1995
(Continued)

*Primary Examiner* — Pedro Philogene
(74) *Attorney, Agent, or Firm* — Jacox, Meckstroth & Jenkins

(57) ABSTRACT

A system and method includes a housing dimensioned to be situated between adjacent spinal bones, such as adjacent vertebrae. Screws are provided in one embodiment and are dimensioned or configured to lock against each other to retain the screws and, consequently, the cover in place. Another embodiment illustrates a plurality of plate elements that can be slidably received and locked in the cage. Each of the plate elements are adapted to receive at least one screw and guide the screw at a predetermined angle into a vertebra, thereby securing the cage in an inter-vertebral space.

66 Claims, 22 Drawing Sheets

Related U.S. Application Data 7,655,028, which is a division of application No. 10/675,361, filed on Sep. 30, 2003, now Pat. No. 7,182,782, application No. 13/409,377, which is a continuation of application No. 10/858,629, filed on Jun. 2, 2004, now Pat. No. 7,641,701.

(51) Int. Cl.

| | | |
|---|---|---|
| *A61B 17/80* | (2006.01) | |
| *F16B 39/10* | (2006.01) | |
| *A61B 17/86* | (2006.01) | |
| *A61F 2/30* | (2006.01) | |
| *A61F 2/28* | (2006.01) | |
| *F16B 41/00* | (2006.01) | |
| *A61F 2/46* | (2006.01) | |

(52) U.S. Cl.
CPC .............. *A61B17/8057* (2013.01); *A61F 2/44* (2013.01); *A61F 2/447* (2013.01); *A61F 2/4465* (2013.01); *F16B 39/101* (2013.01); *A61B 17/8605* (2013.01); *A61F 2/30744* (2013.01); *A61F 2002/2835* (2013.01); *A61F 2002/305* (2013.01); *A61F 2002/30062* (2013.01); *A61F 2002/30131* (2013.01); *A61F 2002/30189* (2013.01); *A61F 2002/30383* (2013.01); *A61F 2002/30385* (2013.01); *A61F 2002/30387* (2013.01); *A61F 2002/30398* (2013.01); *A61F 2002/30439* (2013.01); *A61F 2002/30505* (2013.01); *A61F 2002/30507* (2013.01); *A61F 2002/30517* (2013.01); *A61F 2002/30576* (2013.01); *A61F 2002/30578* (2013.01); *A61F 2002/30604* (2013.01); *A61F 2002/30616* (2013.01); *A61F 2002/30774* (2013.01); *A61F 2002/30784* (2013.01); *A61F 2002/30785* (2013.01); *A61F 2002/30787* (2013.01); *A61F 2002/30794* (2013.01); *A61F 2002/30904* (2013.01); *A61F 2002/449* (2013.01); *A61F 2002/4475* (2013.01); *A61F 2002/4629* (2013.01); *A61F 2310/00017* (2013.01); *A61F 2310/00023* (2013.01); *A61F 2310/00161* (2013.01); *F16B 41/002* (2013.01)

(56) References Cited

U.S. PATENT DOCUMENTS

| | | | |
|---|---|---|---|
| 2,677,369 A | 5/1954 | Knowles | |
| 3,848,601 A | 11/1974 | Ma et al. | |
| 3,867,728 A | 2/1975 | Stubstad et al. | |
| 4,157,715 A | 6/1979 | Westerhoff | |
| 4,309,777 A | 1/1982 | Patil | |
| 4,349,921 A | 9/1982 | Kuntz | |
| 4,488,543 A | 12/1984 | Tornier | |
| 4,553,273 A | 11/1985 | Wu | |
| 4,599,086 A | 7/1986 | Doty | |
| 4,611,581 A | 9/1986 | Steffee | |
| 4,696,290 A | 9/1987 | Steffee | |
| 4,714,469 A | 12/1987 | Kenna | |
| 4,743,256 A | 5/1988 | Brantigan | |
| 4,759,766 A | 7/1988 | Buettner-Janz et al. | |
| 4,834,757 A | 5/1989 | Brantigan | |
| 4,878,915 A | 11/1989 | Brantigan | |
| 4,904,261 A | 2/1990 | Dove et al. | |
| 4,988,349 A | 1/1991 | Pennig | |
| 4,997,432 A | 3/1991 | Keller | |
| 5,041,113 A | 8/1991 | Biedermann et al. | |
| 5,084,049 A | 1/1992 | Asher et al. | |
| 5,085,660 A | 2/1992 | Lin | |
| 5,192,327 A | 3/1993 | Brantigan | |
| 5,246,443 A | 9/1993 | Mai | |
| 5,261,911 A | 11/1993 | Carl | |
| 5,290,312 A | 3/1994 | Kojimoto et al. | |
| 5,324,290 A | 6/1994 | Zdeblick et al. | |
| 5,330,473 A | 7/1994 | Howland | |
| 5,364,399 A | 11/1994 | Lowery et al. | |
| 5,405,391 A | 4/1995 | Hednerson et al. | |
| 5,425,772 A | 6/1995 | Brantigan | |
| 5,439,463 A | 8/1995 | Lin | |
| 5,549,612 A | 8/1996 | Yapp et al. | |
| 5,554,191 A | 9/1996 | Lahille et al. | |
| 5,601,551 A | 2/1997 | Taylor et al. | |
| 5,601,553 A | 2/1997 | Trebing et al. | |
| 5,609,635 A * | 3/1997 | Michelson | 623/17.16 |
| 5,609,637 A | 3/1997 | Biedermann et al. | |
| 5,616,142 A | 4/1997 | Yuan et al. | |
| 5,616,144 A | 4/1997 | Yapp et al. | |
| 5,620,443 A | 4/1997 | Gertzbein et al. | |
| 5,672,177 A | 9/1997 | Seldin | |
| 5,681,310 A | 10/1997 | Yuan et al. | |
| 5,681,311 A | 10/1997 | Foley et al. | |
| 5,702,395 A | 12/1997 | Hopf | |
| 5,713,899 A | 2/1998 | Marnay et al. | |
| 5,713,900 A | 2/1998 | Benzel et al. | |
| 5,716,415 A | 2/1998 | Steffee | |
| 5,720,746 A | 2/1998 | Soubeiran | |
| 5,776,196 A | 7/1998 | Matsuzaki et al. | |
| 5,843,082 A | 12/1998 | Yuan et al. | |
| 5,876,402 A | 3/1999 | Errico et al. | |
| 5,888,228 A | 3/1999 | Knothe et al. | |
| 5,904,683 A | 5/1999 | Pohndorf et al. | |
| 5,925,047 A | 7/1999 | Errico et al. | |
| 5,951,558 A | 9/1999 | Fiz | |
| 5,954,722 A | 9/1999 | Bono | |
| 6,030,389 A | 2/2000 | Wagner et al. | |
| 6,066,175 A | 5/2000 | Henderson et al. | |
| 6,106,557 A | 8/2000 | Robioneck et al. | |
| 6,136,002 A | 10/2000 | Shih et al. | |
| 6,139,550 A | 10/2000 | Michelson | |
| 6,152,927 A | 11/2000 | Farris et al. | |
| 6,159,211 A | 12/2000 | Boriani et al. | |
| 6,159,213 A | 12/2000 | Rogozinski | |
| 6,159,245 A | 12/2000 | Meriwether et al. | |
| 6,171,307 B1 | 1/2001 | Orlich | |
| 6,193,721 B1 | 2/2001 | Michelson | |
| D440,311 S | 4/2001 | Michelson | |
| 6,224,602 B1 | 5/2001 | Hayes | |
| 6,235,033 B1 | 5/2001 | Brace et al. | |
| 6,235,034 B1 | 5/2001 | Bray | |
| 6,235,059 B1 | 5/2001 | Benezech et al. | |
| 6,245,108 B1 | 6/2001 | Biscup | |
| 6,258,089 B1 | 7/2001 | Campbell et al. | |
| 6,261,291 B1 | 7/2001 | Talaber et al. | |
| 6,261,586 B1 | 7/2001 | McKay | |
| 6,264,655 B1 | 7/2001 | Pisharodi | |
| 6,293,949 B1 | 9/2001 | Justis et al. | |
| D449,692 S | 10/2001 | Michelson | |
| 6,306,136 B1 | 10/2001 | Baccelli | |
| 6,306,139 B1 | 10/2001 | Fuentes | |
| 6,328,738 B1 | 12/2001 | Suddaby | |
| 6,361,537 B1 | 3/2002 | Anderson | |
| 6,368,351 B1 | 4/2002 | Glenn et al. | |
| 6,371,986 B1 | 4/2002 | Bagby | |
| 6,383,186 B1 | 5/2002 | Michelson | |
| 6,398,783 B1 | 6/2002 | Michelson | |
| 6,413,259 B1 | 7/2002 | Lyons et al. | |
| 6,416,528 B1 | 7/2002 | Michelson | |
| 6,428,542 B1 | 8/2002 | Michelson | |
| 6,432,106 B1 | 8/2002 | Fraser | |
| 6,454,769 B2 | 9/2002 | Wagner et al. | |
| 6,454,771 B1 | 9/2002 | Michelson | |
| 6,485,517 B1 | 11/2002 | Michelson | |
| 6,503,250 B2 | 1/2003 | Paul | |
| 6,527,776 B1 | 3/2003 | Michelson | |
| 6,533,786 B1 | 3/2003 | Needham et al. | |
| 6,558,423 B1 | 5/2003 | Michelson | |
| 6,558,424 B2 | 5/2003 | Thalgott | |
| 6,569,201 B2 | 5/2003 | Moumene et al. | |
| 6,572,619 B2 | 6/2003 | Santilli | |
| 6,575,975 B2 | 6/2003 | Brace et al. | |
| 6,592,586 B1 | 7/2003 | Michelson | |

(56) References Cited

U.S. PATENT DOCUMENTS

| | | |
|---|---|---|
| 6,599,290 B2 | 7/2003 | Bailey et al. |
| 6,602,256 B1 | 8/2003 | Hayes |
| 6,602,257 B1 | 8/2003 | Thramann |
| 6,605,090 B1 | 8/2003 | Trieu et al. |
| 6,613,053 B1 | 9/2003 | Collins et al. |
| 6,616,666 B1 | 9/2003 | Michelson |
| 6,620,163 B1 | 9/2003 | Michelson |
| 6,626,907 B2 | 9/2003 | Tokish, Jr. et al. |
| 6,652,525 B1 | 11/2003 | Assaker et al. |
| 6,669,700 B1 | 12/2003 | Farris et al. |
| 6,676,703 B2 | 1/2004 | Biscup |
| 6,679,883 B2 | 1/2004 | Hawkes et al. |
| 6,699,249 B2 | 3/2004 | Schlapfer et al. |
| 6,712,818 B1 | 3/2004 | Michelson |
| 6,730,127 B2 | 5/2004 | Michelson |
| 6,755,833 B1 | 6/2004 | Paul et al. |
| 6,776,781 B1 | 8/2004 | Uwaydah |
| 6,776,798 B2 | 8/2004 | Camino et al. |
| 6,835,206 B2 | 12/2004 | Jackson |
| 6,837,905 B1 | 1/2005 | Lieberman |
| 6,852,113 B2 | 2/2005 | Nathanson et al. |
| 6,890,334 B2 | 5/2005 | Brace |
| 6,916,320 B2 | 7/2005 | Michelson |
| 6,926,737 B2 | 8/2005 | Jackson |
| 6,936,050 B2 | 8/2005 | Michelson |
| 6,936,051 B2 | 8/2005 | Michelson |
| 6,964,664 B2 | 11/2005 | Freid et al. |
| 6,969,390 B2 | 11/2005 | Michelson |
| 7,001,387 B2 | 2/2006 | Farris et al. |
| 7,033,394 B2 | 4/2006 | Michelson |
| 7,041,105 B2 | 5/2006 | Michelson |
| 7,041,135 B2 | 5/2006 | Michelson |
| 7,044,952 B2 | 5/2006 | Michelson |
| 7,060,097 B2 | 6/2006 | Fraser et al. |
| 7,074,221 B2 | 7/2006 | Michelson |
| 7,077,843 B2 | 7/2006 | Thramann et al. |
| 7,097,645 B2 | 8/2006 | Michelson |
| 7,112,202 B2 | 9/2006 | Michelson |
| 7,112,222 B2 * | 9/2006 | Fraser et al. ............... 623/17.11 |
| 7,115,130 B2 | 10/2006 | Michelson |
| 7,118,573 B2 | 10/2006 | Michelson |
| 7,137,984 B2 | 11/2006 | Michelson |
| 7,163,561 B2 | 1/2007 | Michelson |
| 7,182,782 B2 * | 2/2007 | Kirschman ............... 623/17.11 |
| 7,186,256 B2 | 3/2007 | Michelson |
| 7,201,753 B2 | 4/2007 | Schlapfer et al. |
| 7,229,477 B2 | 6/2007 | Biscup |
| 7,232,463 B2 * | 6/2007 | Falahee ............... 623/17.11 |
| 7,255,699 B2 | 8/2007 | Paul |
| 7,303,564 B2 | 12/2007 | Freid et al. |
| 7,399,301 B2 | 7/2008 | Michelson |
| 7,503,933 B2 | 3/2009 | Michelson |
| 7,537,603 B2 | 5/2009 | Huebner et al. |
| 7,594,931 B2 | 9/2009 | Louis et al. |
| 7,611,527 B2 | 11/2009 | Freid et al. |
| 7,637,951 B2 | 12/2009 | Michelson |
| 7,637,954 B2 | 12/2009 | Michelson |
| 7,662,154 B2 | 2/2010 | Ribeiro |
| 7,780,708 B2 | 8/2010 | Morris et al. |
| 7,846,190 B2 | 12/2010 | Ball |
| 7,955,362 B2 | 6/2011 | Erickson et al. |
| 8,062,367 B2 | 11/2011 | Kirschman |
| 8,088,163 B1 | 1/2012 | Kleiner |
| 8,182,539 B2 | 5/2012 | Tyber et al. |
| 8,343,223 B2 | 1/2013 | Bucci |
| 8,372,152 B2 | 2/2013 | Kirschman |
| 8,795,370 B2 * | 8/2014 | Kirschman ............... 623/17.11 |
| 2002/0004683 A1 | 1/2002 | Michelson |
| 2002/0045898 A1 | 4/2002 | Freid et al. |
| 2002/0058939 A1 | 5/2002 | Wagner et al. |
| 2002/0120273 A1 | 8/2002 | Needham et al. |
| 2002/0138146 A1 | 9/2002 | Jackson |
| 2002/0143400 A1 | 10/2002 | Biscup |
| 2002/0173790 A1 | 11/2002 | Chang et al. |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0018335 A1 | 1/2003 | Michelson |
| 2003/0023307 A1 | 1/2003 | Michelson |
| 2003/0045880 A1 | 3/2003 | Michelson |
| 2003/0060828 A1 | 3/2003 | Michelson |
| 2003/0078668 A1 | 4/2003 | Michelson |
| 2003/0093082 A1 | 5/2003 | Campbell et al. |
| 2003/0105462 A1 | 6/2003 | Haider |
| 2003/0181912 A1 | 9/2003 | Michelson |
| 2003/0187443 A1 | 10/2003 | Lauryssen et al. |
| 2003/0191471 A1 | 10/2003 | Michelson |
| 2003/0191472 A1 | 10/2003 | Michelson |
| 2003/0199876 A1 | 10/2003 | Brace et al. |
| 2003/0199983 A1 | 10/2003 | Michelson |
| 2003/0208204 A1 | 11/2003 | Bailey et al. |
| 2003/0225409 A1 | 12/2003 | Freid et al. |
| 2004/0019353 A1 | 1/2004 | Freid et al. |
| 2004/0030338 A1 | 2/2004 | Paul |
| 2004/0092939 A1 | 5/2004 | Freid et al. |
| 2004/0097934 A1 | 5/2004 | Farris et al. |
| 2004/0122426 A1 | 6/2004 | Michelson |
| 2004/0127897 A1 | 7/2004 | Freid et al. |
| 2004/0127901 A1 | 7/2004 | Huebner et al. |
| 2004/0127903 A1 | 7/2004 | Schlapfer et al. |
| 2004/0133205 A1 | 7/2004 | Thramann et al. |
| 2004/0181226 A1 | 9/2004 | Michelson |
| 2004/0181229 A1 | 9/2004 | Michelson |
| 2004/0186476 A1 | 9/2004 | Michelson |
| 2004/0193269 A1 | 9/2004 | Fraser et al. |
| 2004/0193270 A1 | 9/2004 | DiMauro et al. |
| 2004/0193271 A1 | 9/2004 | Fraser et al. |
| 2004/0199254 A1 | 10/2004 | Louis et al. |
| 2004/0210313 A1 | 10/2004 | Michelson |
| 2004/0210314 A1 | 10/2004 | Michelson |
| 2004/0230309 A1 | 11/2004 | DiMauro et al. |
| 2005/0038513 A1 | 2/2005 | Michelson |
| 2005/0096657 A1 | 5/2005 | Autericque et al. |
| 2005/0187551 A1 | 8/2005 | Orbay et al. |
| 2005/0251137 A1 | 11/2005 | Ball |
| 2006/0195100 A1 | 8/2006 | Kirschman |
| 2007/0043366 A1 | 2/2007 | Pfefferle et al. |
| 2007/0106388 A1 | 5/2007 | Michelson |
| 2007/0123885 A1 | 5/2007 | Kirschman |
| 2007/0162013 A1 | 7/2007 | Jacene et al. |
| 2008/0021476 A1 | 1/2008 | Kirschman |
| 2008/0097444 A1 | 4/2008 | Erickson et al. |
| 2009/0036985 A1 | 2/2009 | Whiting |
| 2009/0234359 A1 | 9/2009 | Onoue et al. |
| 2010/0070037 A1 | 3/2010 | Parry et al. |
| 2010/0106249 A1 | 4/2010 | Tyber et al. |
| 2011/0015745 A1 | 1/2011 | Bucci |
| 2011/0040382 A1 | 2/2011 | Muhanna |
| 2013/0006367 A1 | 1/2013 | Bucci |

FOREIGN PATENT DOCUMENTS

| | | |
|---|---|---|
| CA | 2163243 A1 | 9/1995 |
| CA | 2383634 A1 | 8/2001 |
| DE | 1139331 A1 | 11/1962 |
| DE | 4409833 A1 | 10/1995 |
| EP | 0179695 A1 | 4/1986 |
| EP | 0307241 A2 | 3/1989 |
| EP | 0599640 A1 | 6/1994 |
| EP | 1169971 A2 | 1/2001 |
| EP | 1437105 A1 | 7/2004 |
| FR | 2727005 A1 | 5/1996 |
| FR | 2827150 A1 | 1/2003 |
| GB | 0401362.9 A1 | 1/2004 |
| WO | 89/09035 A1 | 10/1989 |
| WO | 97/20526 A1 | 6/1997 |
| WO | 99/63914 A1 | 12/1999 |
| WO | 00/66044 A1 | 11/2000 |
| WO | 00/66045 A1 | 11/2000 |
| WO | 02/03885 A2 | 1/2002 |

(56) References Cited

FOREIGN PATENT DOCUMENTS

| WO | 03005939 A2 | 1/2003 | | |
| WO | 2004086990 A1 | 10/2004 | | |
| WO | 2005/070346 A1 | 8/2005 | | |
| WO | 2005070346 | 8/2005 | | |
| WO | WO2008/065443 | * 6/2008 | ................ | 623/17.11 |
| WO | WO 2008065443 | 6/2008 | | |
| WO | WO2011/008864 | * 1/2011 | ................ | 623/17.11 |
| WO | WO 2011008864 | 1/2011 | | |

* cited by examiner

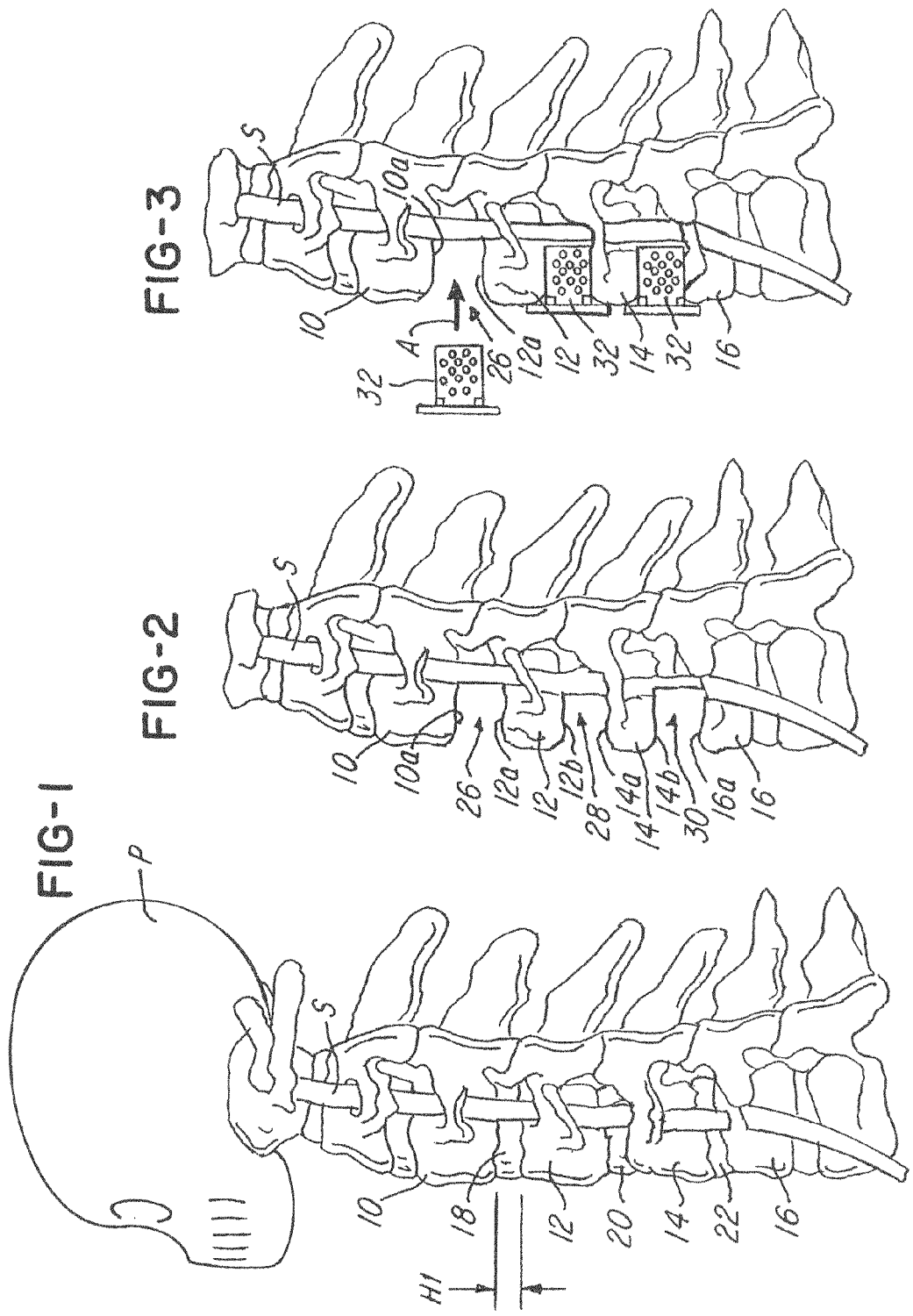

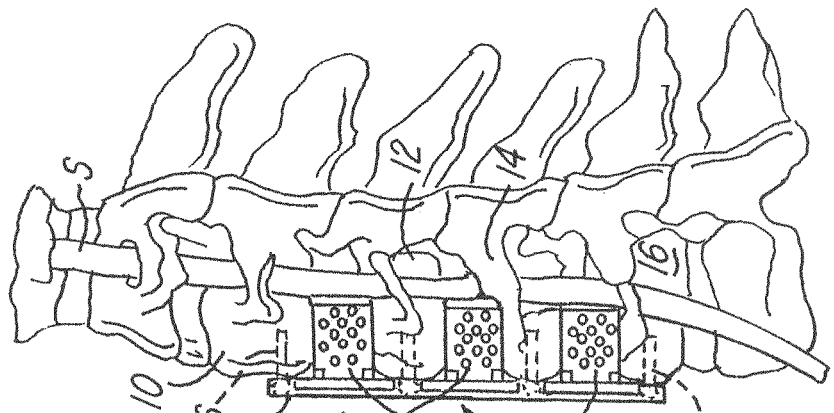
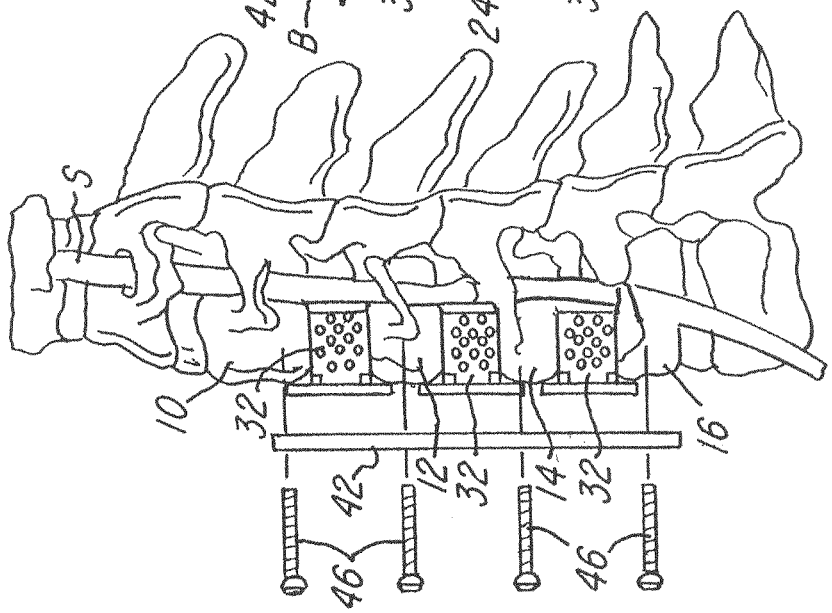
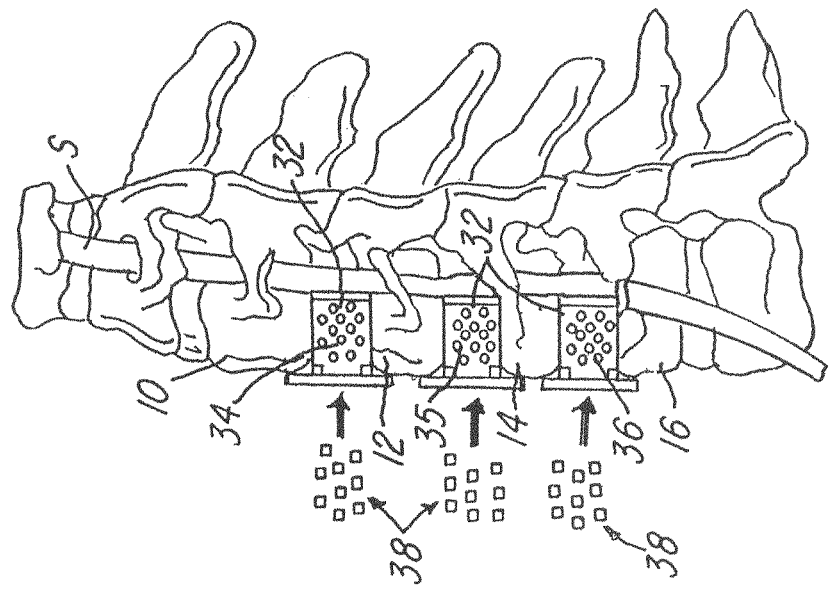

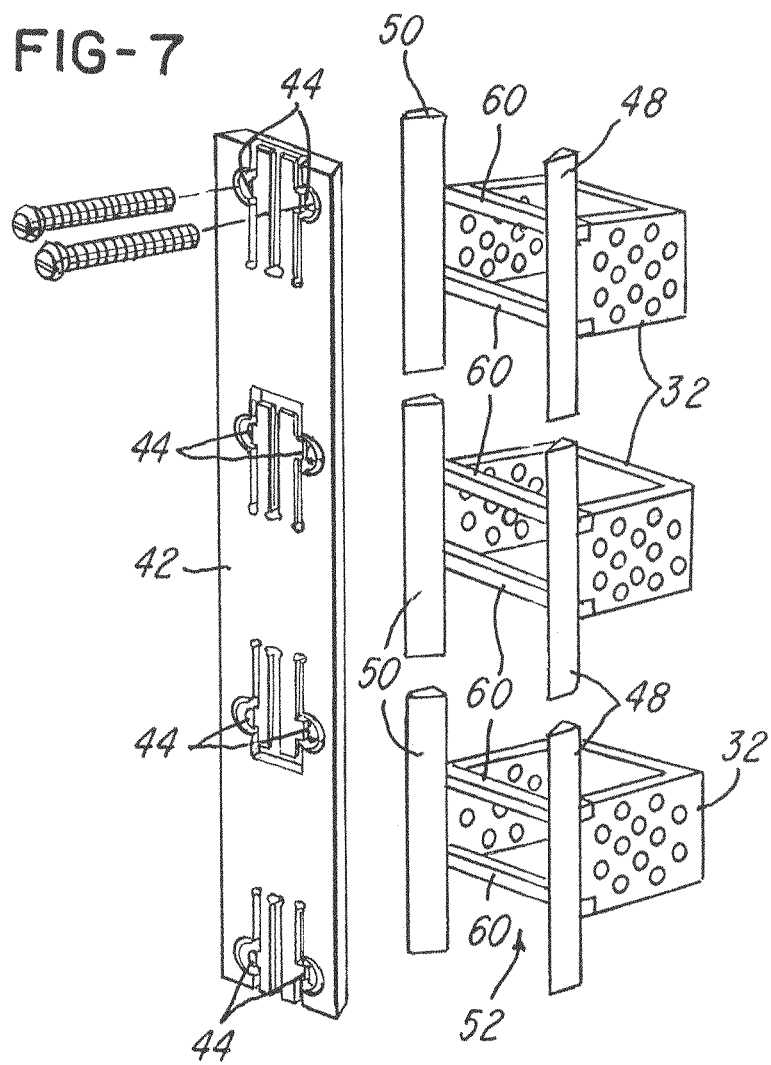

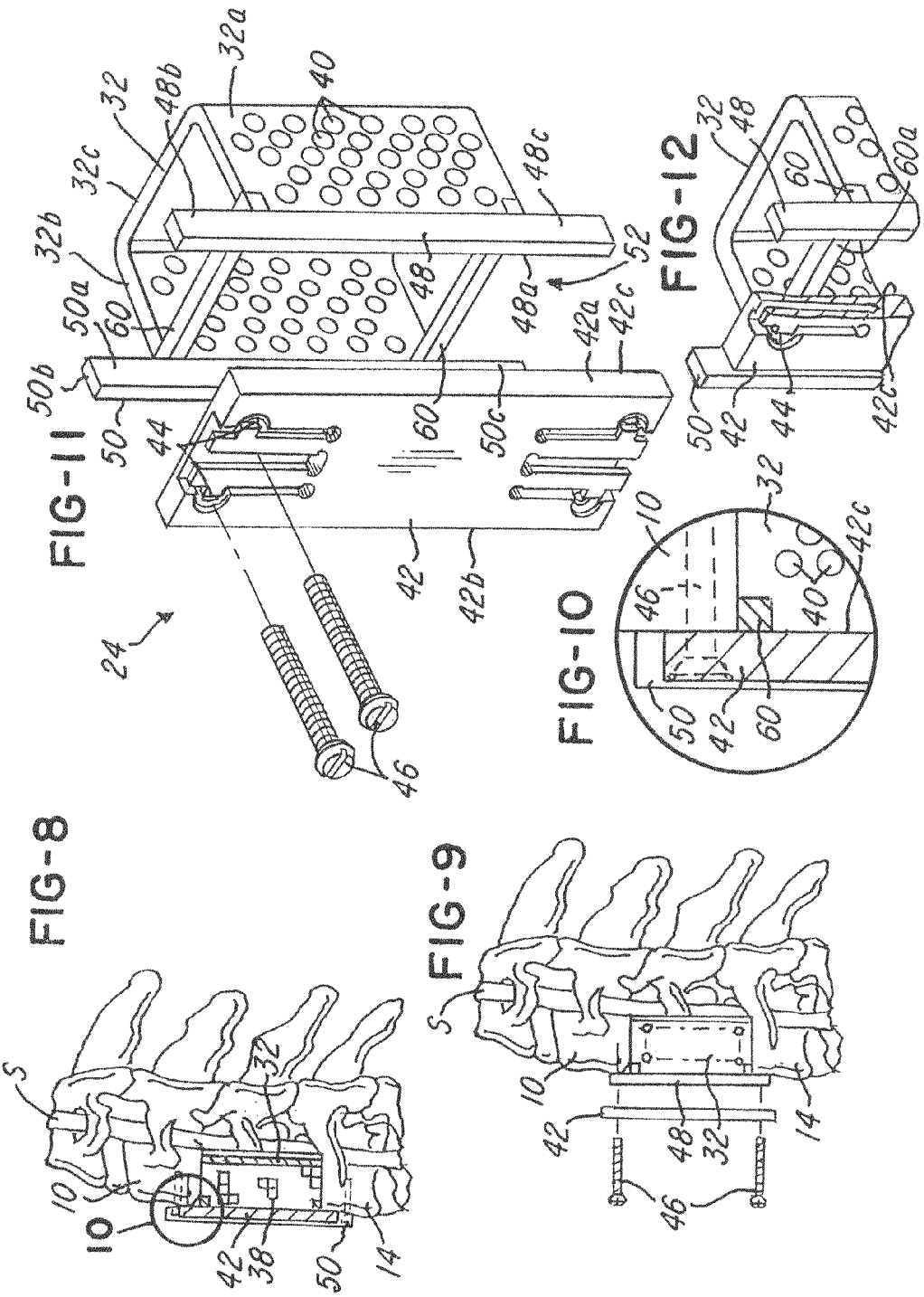

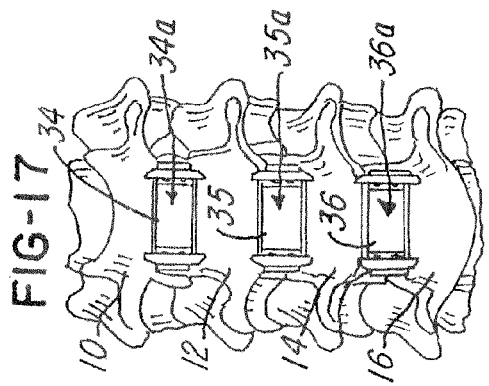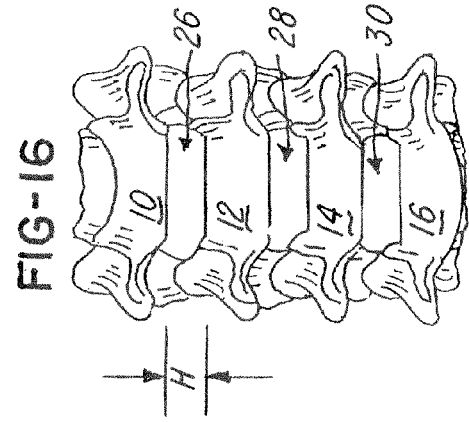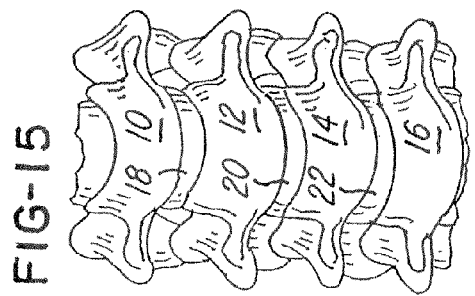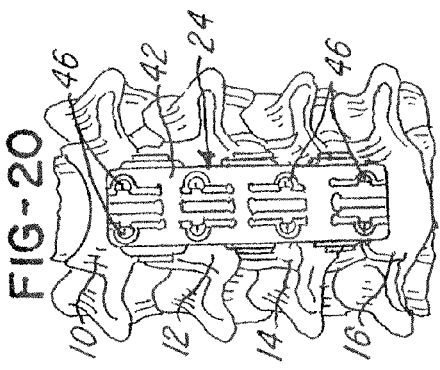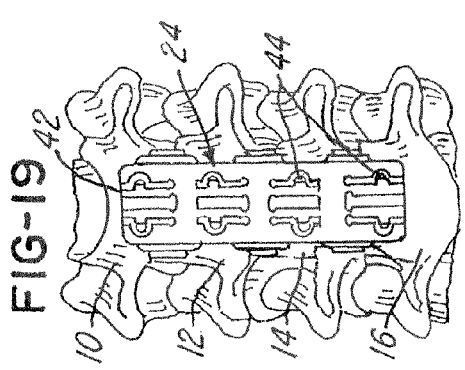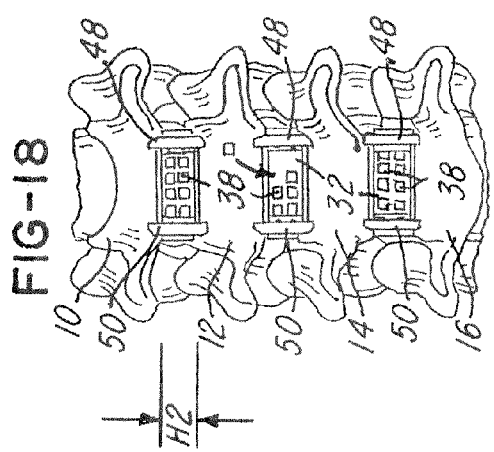

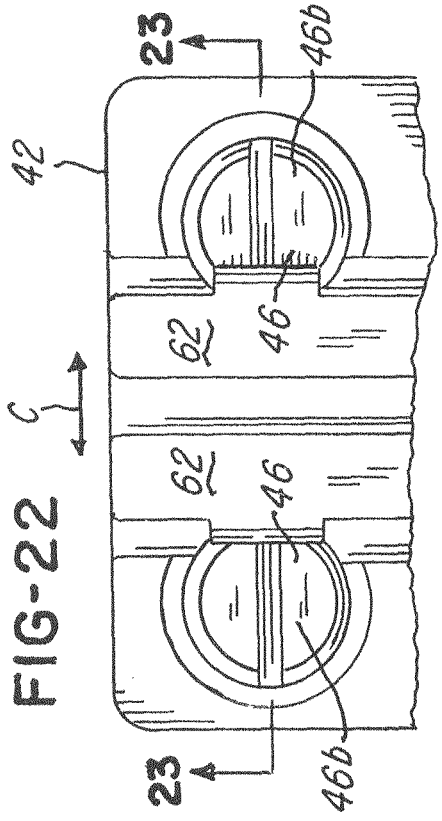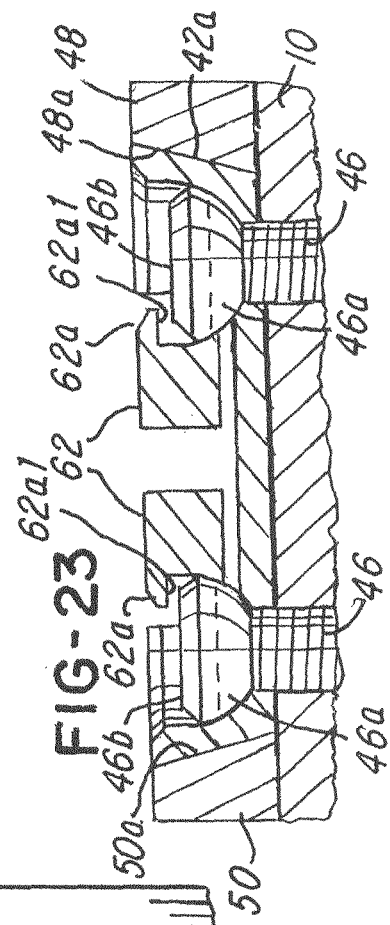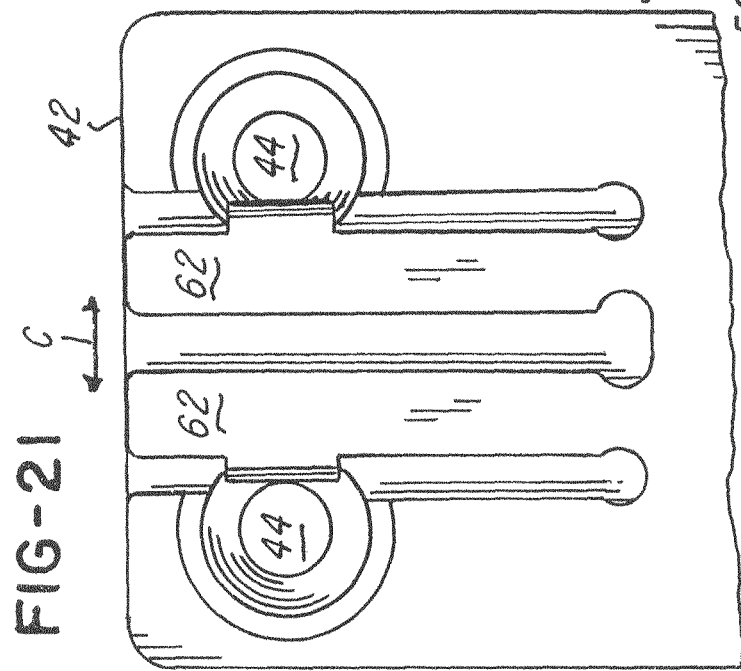

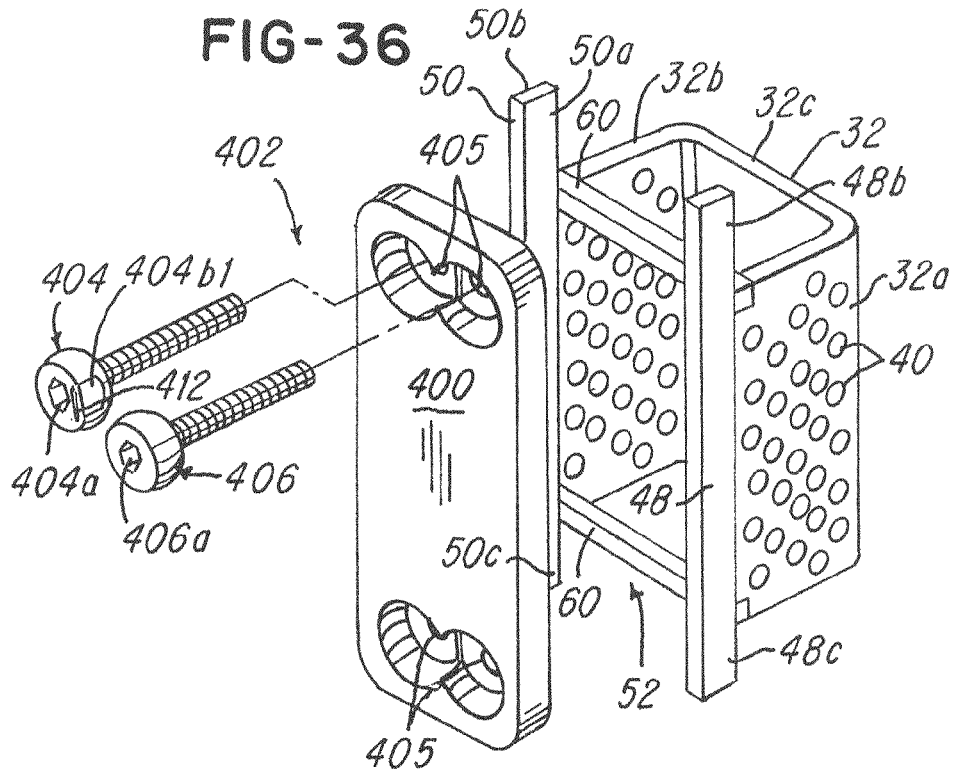
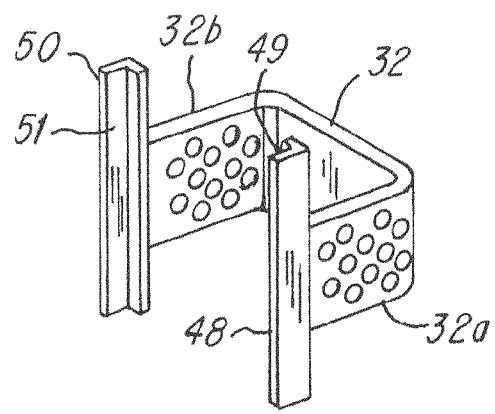

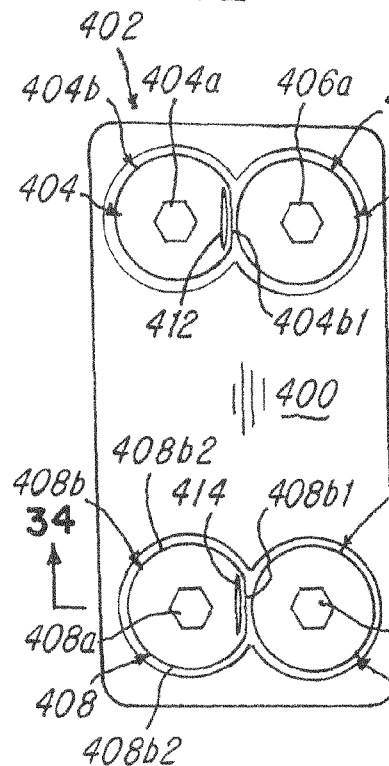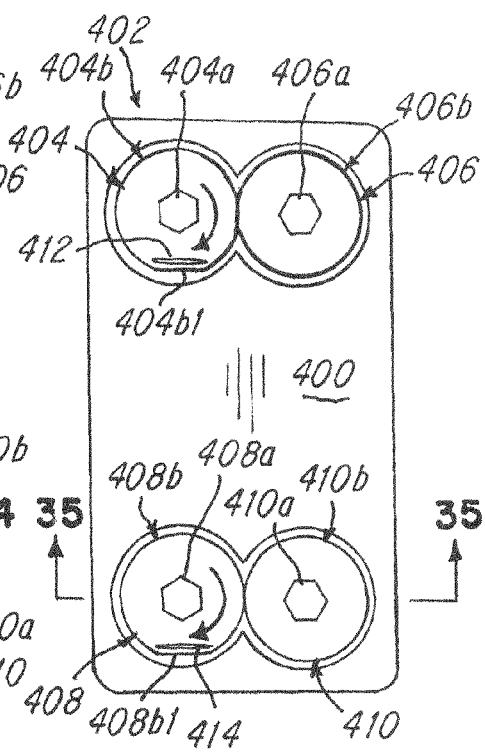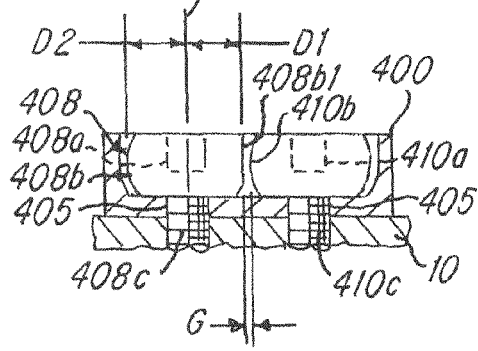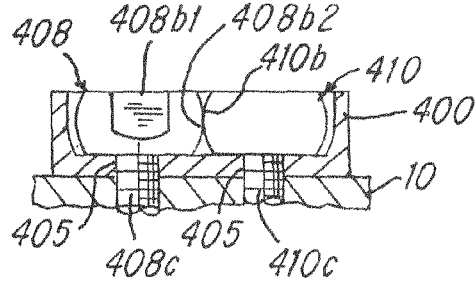

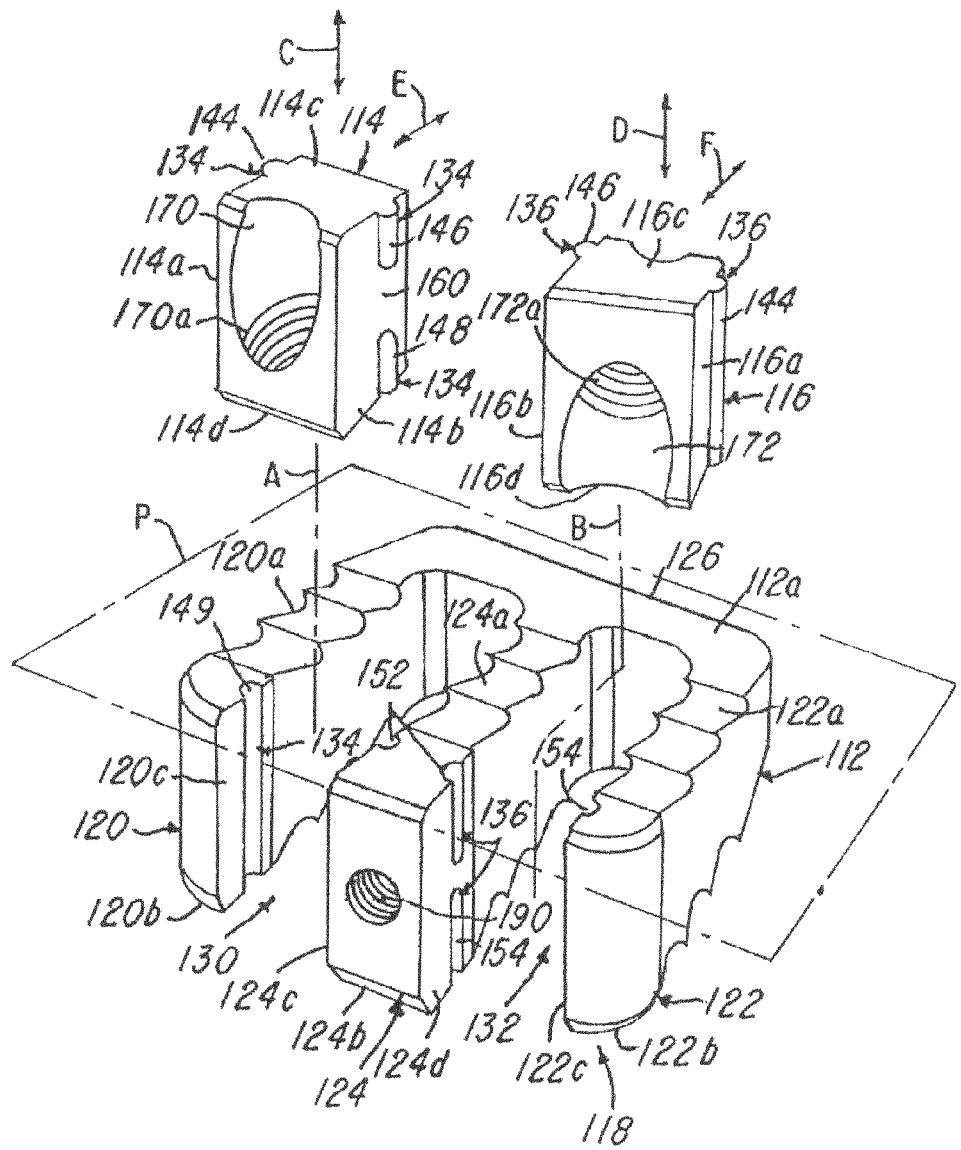

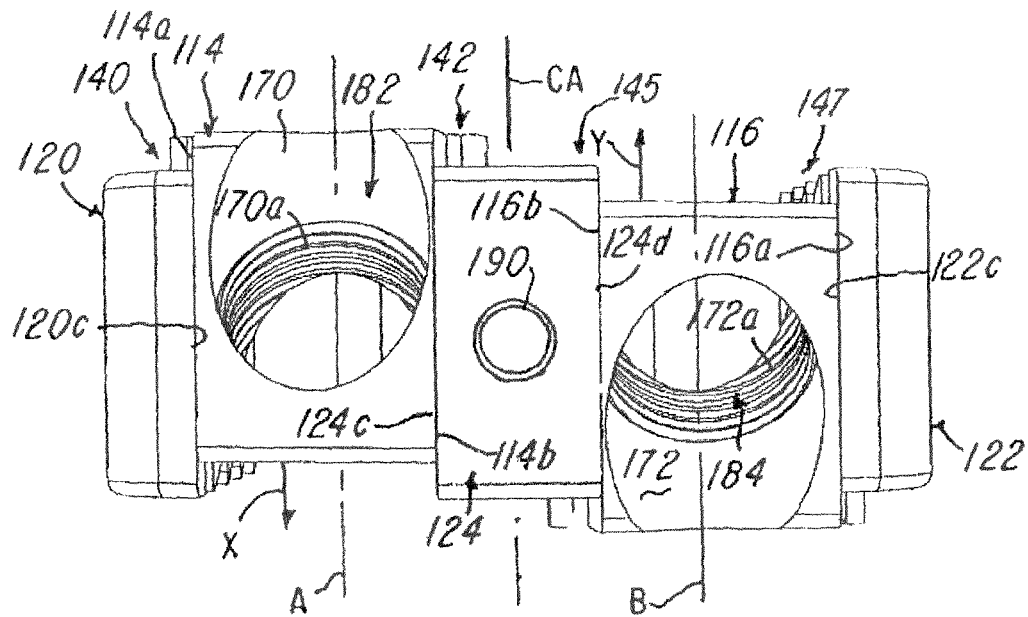
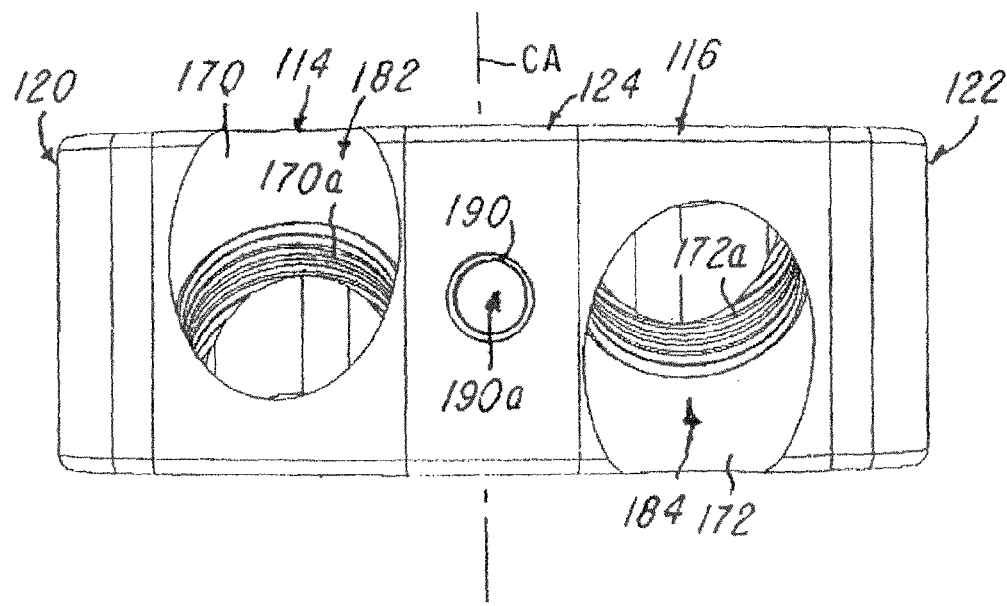

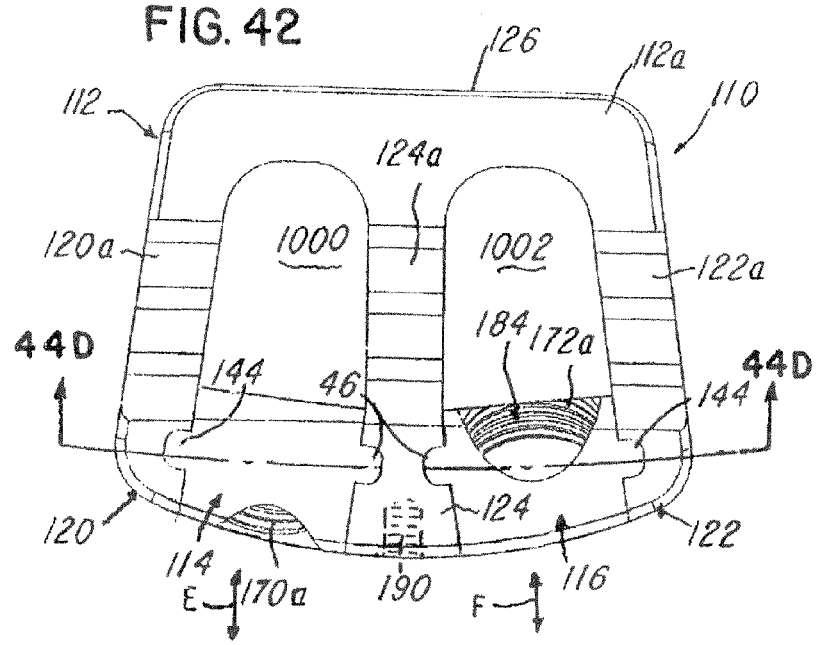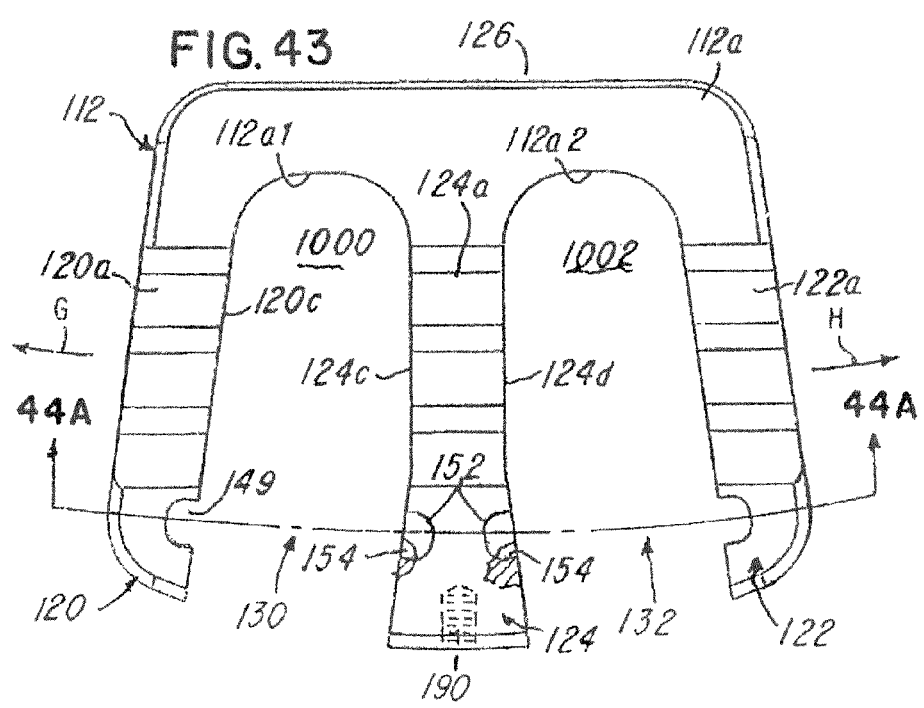

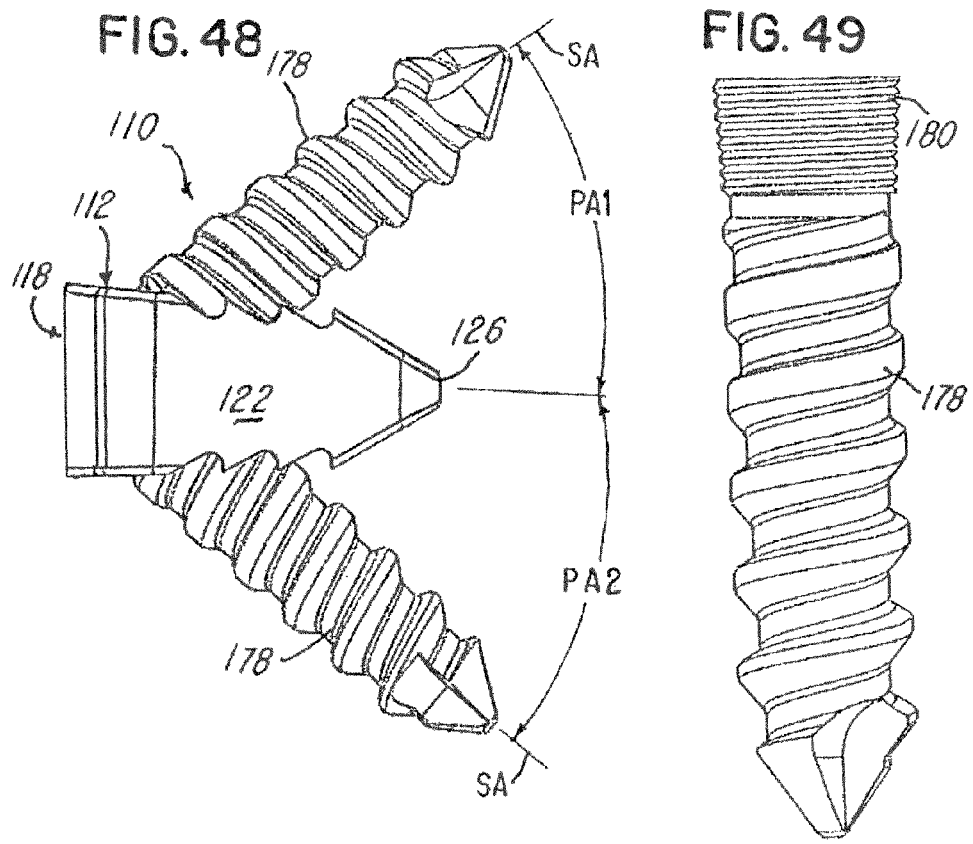
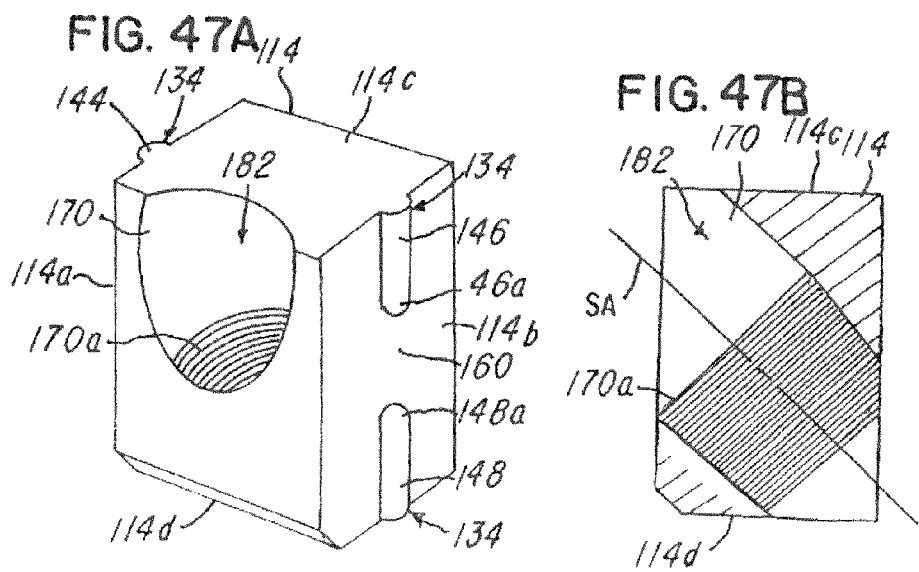

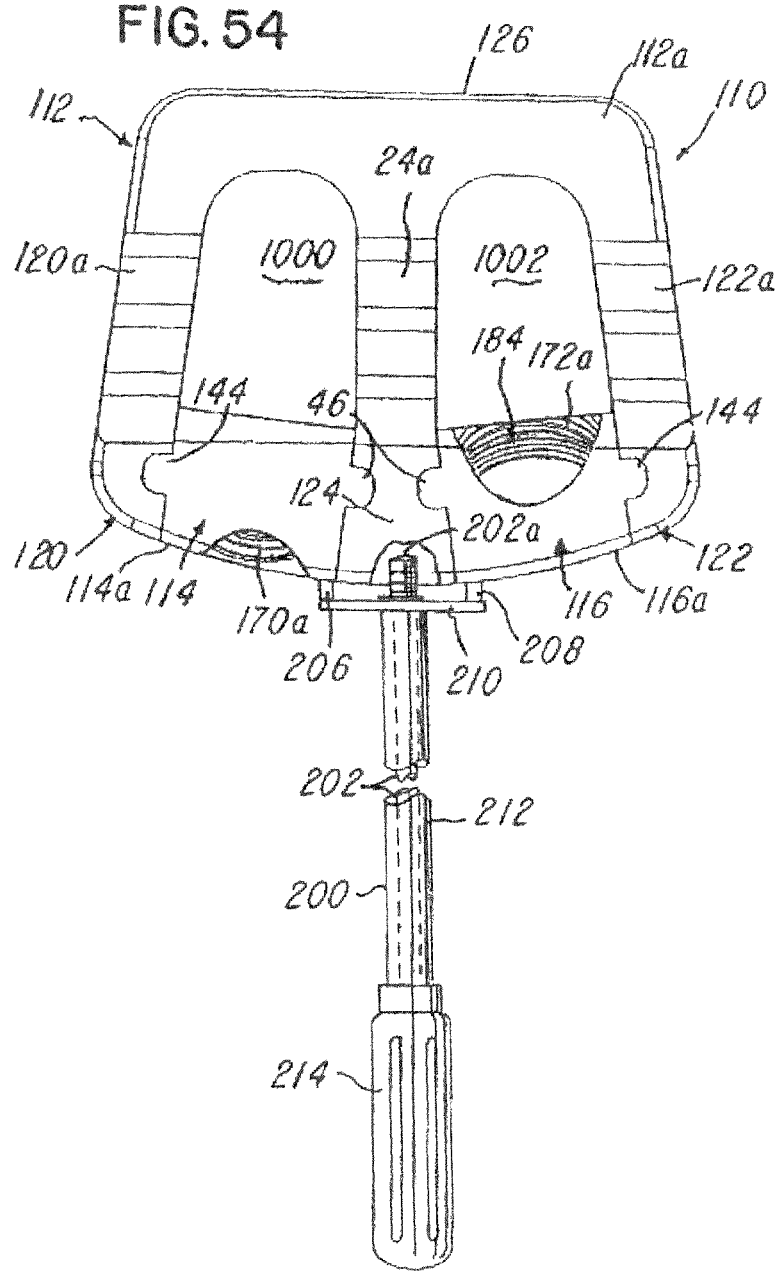

INTERVERTEBRAL FUSION DEVICE UTILIZING MULTIPLE MOBILE UNIAXIAL AND BIDIRECTIONAL SCREW INTERFACE PLATES

CROSS REFERENCE TO RELATED APPLICATIONS

This application is a continuation-in-part of U.S. patent application Ser. No. 12/640,061 filed Dec. 17, 2009, which is a continuation-in-part of U.S. patent application Ser. No. 11/624,341 filed Jan. 18, 2007, now issued as U.S. Pat. No. 7,655,028, which is a division of U.S. patent application Ser. No. 10/675,361, filed Sep. 30, 2003, now issued as U.S. Pat. No. 7,182,782, all of which are incorporated herein by reference and made a part hereof. This application is also a continuation of U.S. patent application Ser. No. 10/858,629, filed Jun. 2, 2004, now issued as U.S. Pat. No. 7,641,701, which is a continuation-in-part of U.S. patent application Ser. No. 10/675,361, filed Sep. 30, 2003, now issued as U.S. Pat. No. 7,182,782, all of which are incorporated herein by reference and made a part hereof.

BACKGROUND OF THE INVENTION

1. Field of the Invention

This invention relates to a veritable prosthetic system and device and a method for implanting the device and, more particularly, to a spinal fusion system and method for fusing spinal bones. This invention also relates to a surgical implant that is used, in its preferred embodiment, for the support of spinal vertebrae. The implant comprises a cage element, at least two independent screw-traversing plate elements, and at least two screw elements, which are placed between the bodies of vertebrae in a surgical procedure. The implant further comprises a mechanism by which each screw-traversing plate element can independently move axially with respect to the cage element and at least one other screw-traversing plate element.

2. Description of the Related Art

Many types of prosthetic devices have been proposed in the past. For example, U.S. Pat. No. 5,192,327 to Brantagan concerns a surgical prosthetic modular implant used singularly or stacked together to support and fuse together adjacent vertebrae or to totally or partially replace one or more vertebrae in a vertebral column. Other surgical implant devices and methods are shown in U.S. Pat. Nos. 5,192,327; 5,261,911; 5,713,899; 5,776,196; 6,136,002; 6,159,245; 6,224,602; 6,258,089; 6,261,586; 6,264,655; 6,306,136; 6,328,738; 6,592,586; U.S. Patent Publication Nos. 2006/0195100; 2007/0123885 and 2008/0021476. Some or all of these devices have improved the success rate and have simplified the surgical techniques in inter-body veritable fusion.

Among some of the problems associated with the prior art devices is that after the device is inserted into a patient during a surgical procedure, there was a possibility of retropulsion of the inter-body device and graft material into the spinal cord or other neurological element.

Another problem with the prior art devices is that grafting material, which was inserted into the devices during the surgical procedure, could not easily be inserted from an anterior direction.

Moreover, in some of the prior art devices, the cover, if any, was typically fastened directly to the device and to spinal bones, which prevented the cover from being capable of moving relative to the device. In addition, in devices that used a cover, the cover did not function to both retain the grafting material in the device and simultaneously fix the spinal bones relative to each other.

Another problem with prior art cage systems is that the screws or fasteners which secured the cover onto the cages sometimes had a tendency to unscrew themselves which is undesirable because the graft material may exit the cage or because the cage itself may move. Another problem is that the screws may withdraw, causing injury to local structures by the screws themselves.

The field of spinal implantation burgeons with devices and methods for the achievement of fixation between vertebrae. Commonly, intervertebral "cages" are utilized to contain bone graft material and provide physical support between adjacent vertebrae. Such devices are exemplified by U.S. Pat. No. 6,371,986 to Bagby, and U.S. Pat. No. 5,609,637 to Biedermann. More recently, devices have been developed which provide supplemental fixation, typically in the form of screws, integrated in some manner with the cage. Such supplemental fixation helps to stabilize the device and prevent loosening until a natural bony fusion takes place. Such devices are exemplified by U.S. Pat. No. 4,904,261 to Dove and U.S. Pat. No. 6,432,106 to Fraser.

In designing devices which integrate a cage component and a screw component, a challenge has been the biomechanical forces between these components. After placement of any cage device, a certain amount of settling or axial motion occurs between the cage and the adjacent vertebrae. Such motion is inevitable and even desirable as it places stabilizing compression onto the device. However, if the cage is rigidly affixed to the adjacent vertebrae with integral screws, such axial motion can be problematic. Undesirable outcomes include screw loosening or breakage as settling invariably occurs.

In order to avoid such outcomes, various mechanisms allow for multi-axial motion between the screw and cage components. One problem with this approach is that multi-axial motion will allow for screw rotation within the vertebral body, reducing the effectiveness of fixation. A further disadvantage is that the multi-axial approach prevents a fixed, repeatable screw trajectory to ensure appropriate placement into the adjacent vertebral body.

What is therefore needed is a device incorporating screw-cage interfaces which provide for controlled uni-axial motion which allows for axial settling, but will not produce undesirable rotation within the vertebral body. Furthermore, the system needs to provide a specific, repeatable screw trajectory to ensure appropriate placement into the adjacent vertebral body.

What is needed, therefore, is a system and method, which facilitates overcoming one or more of the aforementioned problems as well as other problems and to provide a device that has unique features that will facilitate reducing the risk associated with neurological surgeries and advance the present state of the art.

SUMMARY OF THE INVENTION

It is, therefore, one object of the invention to provide a spinal fusion system and method which utilizes a housing that can be inserted, but comprises features which, for example, enables the device to float relative to a cover, facilitates retaining any graft material within the device, facilitates fixing a relative relation among or between spinal bones, facilitates providing a cover for covering one or multiple devices, and/or includes locking features that facilitates preventing the screws which secure the cover to the spinal bones from the retracting.

Another object of one embodiment is to provide a plurality of screws that are capable of locking to facilitate preventing the fasteners to become unfastened or unscrewed.

Another object of the invention is to provide fasteners at least one of which has an eccentric to facilitate locking against an adjacent fastener in order to retain the fasteners and the cover in a locked position.

In one aspect, this invention comprises an apparatus for surgical use in humans, comprising a housing for insertion between vertebrae in a human spine, a recess in the housing for receiving bone graft material, a cover securable to at least one of the adjacent vertebrae and being configured to block egress of the bone graft material from the recess, and the cover and the housing being slidably engaged one to the other.

In another aspect, the invention comprises a surgical implant, comprising a housing, a recess in the housing for receiving bone graft material, the housing having an opening in a side thereof, the opening communicating with the recess and being configured for insertion of the bone graft material into the recess, a cover mechanically engaging the housing so as to permit sliding relative movement therebetween, the cover being configured to retain the bone graft material within the recess.

In yet another aspect, the invention comprises a surgical implant for use with human vertebrae, comprising: a generally U-shaped housing defining an opening in an anterior side thereof, a recess in the housing communicating with the opening, the recess being configured for receiving bone graft material, and a cover in locating and mating engagement with the housing, the cover being securable to at least one of the adjacent vertebrae and configured to block egress of the bone graft material from the recess.

In still another aspect, the invention comprises a surgical implant for use with human vertebrae, comprising: a generally U-shaped housing having a plurality of closed sides and an open side defining an opening at an anterior of the housing, the housing being disposable between adjacent vertebrae, a recess in the housing communicating with the opening, the recess extending through superior and inferior portions of the housing and being configured for receiving bone graft material therein, a cover mechanically coupled with the housing so as to permit sliding relative movement therebetween, the cover being disposed over the opening and configured to block egress of the bone graft material from the recess with the cover being securable to at least one of the adjacent vertebrae, and screw-receiving apertures in the cover for accommodating screws securing the cover to the at least one adjacent vertebrae.

In yet another aspect, the invention comprises a method for fusing spinal bones together, comprising the steps of: removing diseased or injured spinal bones and/or vertebral disks, and situating a spinal implant between remaining spinal bones, the spinal implant comprising a housing, a recess in the housing having bone graft material therein and a cover secured to at least one of the remaining spinal bones, the cover blocking egress of the bone graft material from the recess and the cover and the housing being slidably engaged one to the other.

In still another aspect, the invention comprises a method for fusing spinal bones together, comprising the steps of: removing diseased or injured spinal bones and/or vertebral disks, and situating a spinal implant between remaining spinal bones, the spinal implant comprising a generally U-shaped housing having an opening in an anterior side thereof, a recess in the housing having bone graft material therein, and a cover secured to at least one of the remaining spinal bones, the cover blocking egress of the bone graft material from the recess and the cover and being in locating and mating engagement with the housing.

In yet another aspect, another embodiment of the invention comprises a spinal implant comprising a cage having a plurality of windows and a plurality of plate elements, each of the plurality of plate elements having an aperture for receiving a screw, the plurality of plate elements and the cage being adapted to permit the plurality of plate elements to move independently on the cage.

In another aspect, another embodiment of the invention comprises a spinal implant comprising, a cage, a first plate and a second plate, the cage, the first plate and the second plate having a plurality of interfitting joints for permitting the first and second plates to move relative to the cage after the first and second plates are mounted on the cage and a lock or retainer for locking or retaining, respectively, the first and second plates on the cage after they are mounted thereto.

In still another aspect, another embodiment of the invention comprises an apparatus for surgical use in humans, comprising a housing for insertion between vertebrae in a human spine, a recess in the housing for receiving bone graft material, a cover securable to at least one of the adjacent vertebrae and being configured to block egress of the bone graft material from the recess and the cover and the housing being slidably engaged one to the other In another object, this device ideally utilizes multiple screws pointed in opposing directions, each screw-device interface being able or adapted to move independently with respect to the cage component and all other screw or plate components.

These and other objects and advantages will be apparent from the following description, the accompanying drawings and the appended claims.

BRIEF DESCRIPTION OF THE DRAWINGS

FIG. 1 is a partial side view of a human spine illustrating anteriorly discs between various spinal bones;

FIG. 2 is a partial side view of the spinal column shown in FIG. 1 illustrating several of the discs removed, for example, after surgical procedure;

FIG. 3 is a partial side view of the human spine with the housings according to one embodiment of the invention situated therein;

FIG. 4 is a partial side view of the human spinal column illustrating graft material being inserted anteriorly into the housing;

FIG. 5 is a partial exploded side view of the embodiment shown in FIG. 1-4 illustrating a cover and a plurality of screws which will secure the cover to the spinal column;

FIG. 6 is a side view similar to FIG. 5 illustrating after the cover has been mounted to the spinal column;

FIG. 7 is an exploded view of the device shown in FIG. 6, illustrating a plurality of housings and a single cover for use with covering the plurality of housings;

FIG. 8 is partial side view illustrating an elongated housing and cover used during a vertebrectomy procedure;

FIG. 9 is a partial side view of the spinal column illustrated in FIG. 8 showing the elongated housing situated between adjacent spinal bones in a single cover to be affixed to those spinal bones;

FIG. 10 is an exploded view of the circle area shown in FIG. 8;

FIG. 11 is a exploded view of the elongated housing illustrated in FIGS. 8 and 9 and the cover and screws associated therewith;

FIG. 12 is a partial fragmentary view of the cover and housing after the cover has been situated between a pair of rails associated with the housing;

FIG. 15 is a partial anterior side view a human spine illustrating the discs between various spinal bones;

FIG. 16 is a partial anterior view of the spinal column shown in FIG. 1 illustrating several of the discs removed, such as by surgical procedure;

FIG. 17 is a partial anterior view of the human spine with the housings according to one embodiment of the invention situated therein;

FIG. 18 is a partial anterior view of the human spinal column illustrating graft material being inserted anteriorly into the housing;

FIG. 19 is a partial exploded anterior view of the embodiment shown in FIG. 1-4 illustrating a cover and a plurality of screws for securing the cover to the spinal column;

FIG. 20 is a anterior view similar to FIG. 5 illustrating the cover mounted to the spinal column;

FIG. 21 is a fragmentary view illustrating various features of the cover;

FIG. 22 is another fragmentary view of the cover after the screws are mounted and the locking mechanism retains the screws therein;

FIG. 23 is a fragmentary sectional view of the embodiment shown in FIG. 22 illustrating various features of the locking mechanism;

FIG. 31 is a view of a housing having walls having recessed areas for receiving the cover;

FIG. 32 is a view of another embodiment of the invention showing the plurality of fasteners or screws in an unlocked position;

FIG. 33 is a view of the fasteners or screws shown in FIG. 32 in a locked position;

FIG. 34 is a view taken along the line 34-34 in FIG. 32;

FIG. 35 is a view taken along the line 35-35 in FIG. 33;

FIG. 36 is an exploded view of the other embodiment of the invention with the locking screws illustrated in FIGS. 32-35;

FIG. 39 is a view illustrating a cage and a plurality of planar members or plate inserts;

FIG. 40 is a view illustrating the sliding movement of the plate members in the cage;

FIG. 41 is a view illustrating the plate members in a home position;

FIG. 42 is a plan view of the embodiment shown in FIG. 41;

FIG. 43 is a plan view of the embodiment shown in FIG. 41 without the plate elements;

FIG. 47A is a perspective view of the plate element shown in FIGS. 45 and 46,

FIG. 47B is a sectional view illustrating a tapered and threaded bore in the plate element shown in FIG. 47A;

FIG. 48 is a side view of an implant having the plates and screws therein illustrating the predetermined angles at which the screws traverse through the cage;

FIG. 49 is a view of a screw adapted to be used in the cage;

FIG. 54 is a perspective view showing the tool in FIG. 53 mounted on the cage and securing the plates therein.

DETAILED DESCRIPTION OF PREFERRED EMBODIMENTS

Figure 13:
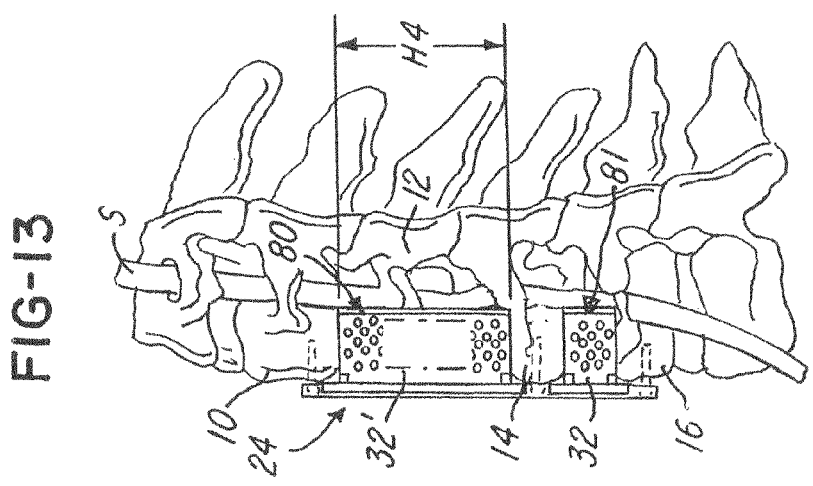
FIG. 13 illustrates a partial side view of an embodiment showing a plurality of housings of different sizes used with a single cover.

Referring now to FIG. 1, a partial side view of a patient or person P is shown having a spinal column S and a plurality of spinal bones, such as vertebrae, 10, 12, 14 and 16. Note that a disc, such as discs 18, 20 and 22 in FIG. 1, is located between adjacent pairs of spinal bones (e.g., between bones 10 and 12, 12 and 14, and 14 and 16). During a spinal fusion procedure, such as a discectomy, the discs 18, 20 and 22 may be removed so that adjacent vertebrae may be fused together FIG. 2 illustrates a fragmentary view of the spinal column S shown in FIG. 1, with the discs 18, 20 and 22 removed. It should also be understood that during another surgical procedure, such as a vertebrectomy, it may be desired to remove part or all of one of the spinal bones 10-16, as illustrated in FIG. 13. In this type of neurological procedure, it may also be desired to fuse adjacent spinal bones together for reasons that are conventionally known. This invention provides means for facilitating and performing such procedures. For ease of illustration, FIGS. 15-20 provide corresponding anterior views to the side views shown in FIGS. 1-6, respectively.

In the embodiment being described, a spinal fusion system 24 is provided for use as a prosthetic implant during a neurological procedure such as the aforementioned vertebrectomy or discectomy. In general, after the discs 18, 20 and 22 (FIG. 1) are removed, as illustrated in FIG. 2, a plurality of receiving areas 26, 28 and 30 (FIGS. 2 and 17) are defined by the areas between the surfaces of adjacent spinal bones 10, 12, 14 and 16. As illustrated in FIG. 2, the area 26 is bounded in part by the surface 10a of spinal bone 10 and surface 12a of spinal bone 12. Likewise, area 28 is partially bounded by surface 12b of spinal bone 12 and surface 14a of spinal bone 14, and area 30 is bounded by surface 14b of spinal bone 14 and surface 16a of spinal bone 16.

As illustrated in FIGS. 3-7 and 11 and as will be described in more detail later herein, the spinal fusion system 24 comprises a housing 32 dimensioned to be situated or received between adjacent spinal bones, such as bones 10 and 12. A housing 32 is situated in each of the plurality of receiving areas 26, 28 and 30, as illustrated in FIGS. 3-4. Each housing 32 cooperates with adjacent spinal bones to define a graft area, such as areas 34, 35 and 36 in the view illustrated in FIG. 17, for receiving graft material 38 (FIGS. 4 and 18). As illustrated in FIGS. 4 and 18, the graft material 38 is situated in the areas 34, 35 and 36 after placement of the housing 32.

As illustrated in FIG. 11, the housing 32 is generally U-shaped as shown. In the embodiment being described, the housing 32 comprises a well 33 defining multiple sides and comprising a predetermined shape selected to cause the graft material to be formed into a multi-sided fused coupling between adjacent spinal bones, such as bones 10 and 12 in FIG. 3. Although not shown, the housing 32 could define a shape other than rectangular, such as semi-circular, oval or other suitable shape as may be desired. Note that the housing 32 comprises a first wall 32a, a second wall 32b and a third wall 32c joining the first wall 32a and the second wall 32b. One or more of the walls 32a-32c may comprise a plurality of holes or apertures 40 which facilitate the fusing process. The apertures 40 also permit visualization of graft material 38 on x-rays.

As mentioned later herein, the predetermined shape defined by the spinal fusion system 24 may provide a fused multi-sided plug of fusion material 38 having a height H (FIGS. 14 and 16) of at least two millimeters, but typically less than approximately 180 millimeters. This height H may vary depending on the vertical size or height H (as viewed in FIG. 16) of the areas 26-30 to be filled. For example, in the area 26 illustrated in FIGS. 2, 14 and 16, the height H of the area 26 generally corresponds to a height H1 (FIG. 1) of a disc, such as disc 18. Thus, the fusion material 38 (FIG. 18) would resultantly have a fused height H2 (FIG. 18) that generally corresponds to the height H (FIG. 16) and height H1 (FIG. 1). If, for example, a housing 32 having a longer height is required, such as height H3 in FIG. 14 and height H4 in FIG. 13, such as in the event of a vertebrectomy, then the fusion system 24 and housing 32 will define a height that generally corresponds to the dimension or height H (FIG. 9) to be traversed. Thus, it should be understood that the dimensions of the generally U-shaped housing 32 of the spinal fusion system 24 is selected depending on the size of the area 26-30 to be filled and the environment or application in which the spinal fusion system 24 is used. In general, the width and depth of the housing 32 will be approximately 9-20 millimeters and 7-20 millimeters, respectively.

As illustrated in FIGS. 5-7, 11, 14 and 21-22, the spinal fusion system 24 further comprises a cover 42 comprising a plurality of apertures 44 that receive a plurality of screws 46, respectively, which are screwed directly into the spinal bones 10 and 16, as illustrated, for example, in FIGS. 5-6.

As illustrated in FIG. 11, the housing 32 comprises a first rail, channel wall or wall portion 48 and a second rail, channel wall or wall portion 50 which cooperate to define a channel area 52 for receiving the cover 42. It should be understood that when the cover 42 is received in the channel area 52, the sides 42a and 42b become associated with the sides 48a and 50a. It should be understood that the cover 42 is not permanently secured to the housing 32 after it is received in channel area 52. This feature permits the housing 32 to migrate or float relative to the cover 42 even after the cover 42 is fixed to one or more of the spinal bones 10-16 as illustrated in FIGS. 6 and 20. As illustrated in FIG. 23, the edges 42a and 42b of cover 42 and sides 48a and 50a may be beveled and complementary to facilitate locating and mating engagement between the cover 42 and housing 32.

As illustrated in FIGS. 3-6 and 16-20, after the graft material 38 is placed in the housing 32 and the graft areas 35-36 (FIG. 17) defined by the housing 32 and adjacent spinal bones, then the cover 42 is situated between the walls or rails 48 and 50, as illustrated in FIGS. 6 and 19. The screws 46 may then be used to secure the cover 42 to one or more of the spinal bones 10-16 as illustrated in FIGS. 6 and 20. It should be understood that a feature of the invention is that the cover 42 facilitates aligning the housings 32 in a substantially co-lineal or relatively aligned position relative to each other and to the spinal bones 10-16, as illustrated in FIGS. 6, 19 and 20. In the setting of multiple level discectomy, the floating cover 42 allows limited, controlled settling of the cages or housings 32 in the vertical plane with respect to the cover 42. As illustrated in FIGS. 6, 8, 10 and 20, the cover 42 also provides means for providing a mechanical fixation of the adjacent spinal bones 10-16 relative to each other. Thus, while the housing 32 cooperates with adjacent spinal bones, such as spinal bones 10 and 12, to define a graft receiving area 34, the cover is multi-functional in that it not only covers the opening of any graft areas, such as area 34 (FIG. 17), but it also secures and retains the spinal bones 10-16 in a fixed spatial relationship relative to each other and relative to the housings 32. It should also be understood that the cover 42 may be fixed to one or more of the spinal bones 10-16 as may be desired to accomplish either of the aforementioned functions.

As illustrated in FIG. 11, note that the walls 48 and 50 further define projections 48b, 48c, 50b and 50c as shown. As illustrated in FIGS. 3-6 and 17-20, the projections 48b, 48c, 50b and 50c provide a plurality of migration preventers for preventing the housing 32 from migrating posteriorly in the direction of arrow A (FIG. 3) toward the spinal cord S or other neurological elements after the housing 32 is situated between the adjacent spinal bones 10-16 as illustrated. Further, the migration preventers 48b, 48c, 50b and 50c enable a surgeon to locate each housing 32 between adjacent spinal bones, such as spinal bones 10-16 in FIG. 1, and move the housing 32 in the direction of arrow A in FIG. 3 until the migration preventers 48b, 48c, 50b and 50c engage the surface 10a of spinal bone 10 and migration preventers 48b, 48c, 50b and 50c engage the surface 12a of spinal bone 12. As illustrated in FIG. 3, after the housings 32 are situated between the spinal bones 10-16 as shown, the migration preventers 48b, 48c, 50b and 50c facilitate preventing the wall 32c from being over-inserted by the surgeon or from being over-inserted to a point where it engages the spinal cord S or other neurological elements.

Figure 26:
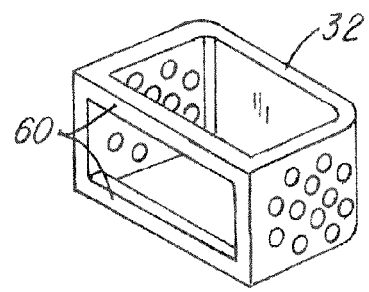
FIG. 26 is a view of another embodiment of the invention showing the crossbars integrally formed in the housing and without migration preventers.

The spinal fusion system 24 further comprises at least one migration stop or crossbar 60 as illustrated in FIGS. 11, 12, 29 and 30. The crossbar 60 may be either integrally formed in housing 32, as shown in FIG. 26, or separate as illustrated in FIGS. 7, 11, 12, 14, 29 and 30, for example. As illustrated in the exploded view in FIGS. 10 and 11, the surface 60a of crossbar 60 engages and cooperates with surface 42c of cover 42 to prevent anterior migration in the direction of arrow B). Thus, the spinal fusion system 24 of the embodiment being described provides means for preventing insertion of the housing 32 to a point where it might engage the spinal cord S (FIG. 3) or other neurological elements, such as dura mater, thecal sac, and also means for facilitating prevention of migration of the housing 32 in an anterior direction or in the direction of arrow B in FIG. 10 after the housing 32 is situated as described herein and the cover 42 is mounted to one or more of the spinal bones 10-16.

Figure 29:
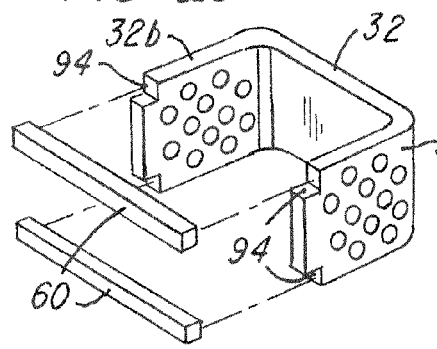
FIG. 29 is another view of the housing illustrating a plurality of removable crossbars without any migration preventers.
Figure 30:
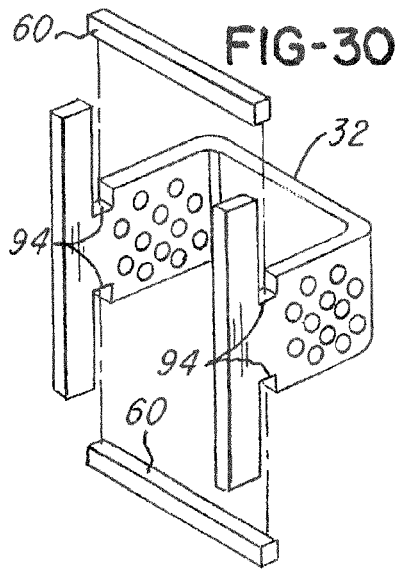
FIG. 30 illustrates another embodiment of the invention, similar to the devices illustrated earlier relative to FIG. 1-20 showing details of the cross bars and notches for receiving them.

It should be understood that a plurality of the migration stops or cross bars 60 may be used alone or in combination with the migration preventers 48b, 48c, 50b and 50c. It should be understood that the stops 60 could be detachable, as shown in FIG. 26, or they could be integrally formed in housing 32 (as shown in FIG. 26). Also, these cross bars 60 may be removably received in the notched receiving areas 94 (FIGS. 29-30). For example, in anatomy that provided limited space, the surgeon may elect not to use a housing with cross bars 60 or use a housing that does not have integrally formed cross bars.

The system 24 further comprises a system or means for preventing retraction or back out of the screws 46 after they are screwed into the spinal bones 10-16 in order to secure the cover 42 thereto. The spinal fusion system 24 of the present invention may be used with conventional screw lock devices or with a unique locking mechanism and system, which will now be described relative to FIGS. 21-23.

As illustrated in FIGS. 21-23, the spinal fusion system 24 and, more particularly, cover 42 may be provided with at least one or a plurality of resilient detents 62 which are generally L-shaped as shown and are resilient so that they can move laterally in the direction of double arrow C in FIGS. 21-22 towards and away from a home position (FIG. 21) to permit the screws 46 first received in the apertures 44, and, second, locked into the cover 42. Thereafter, the screws 46 may be screwed into a spinal bone, such as spinal bone 10, and when a screw head 46a of the screw 46 engages a detent portion 62a of the resilient detent 62, the resilient detent 62 moves in a direction away from the apertures 44 until the screw head 46a clears the portion 62a. After a top surface 46b of the screw head 46a has cleared the bottom surface 62a1 (as viewed in FIG. 23) of portion 62a, the resilient detent 62 moves back toward aperture 44 to the home position until the portion 62a and surface 62a1 are operatively positioned over surface 46b of screw 46, thereby retaining and preventing the screws 46 from backing out of the cover 42 and thereby preventing the screws 46 from backing out of the spinal bone 10.

The plate comprises a first surface 50d (FIG. 23) and a second surface 50e. The plate member further comprises a seat or edge 50f (FIG. 21) associated with the first surface 50d and the detent 62a associated with the second surface 50e.

In the embodiment being described, the components of the spinal fusion system 24, such as the housing 32, first channel wall portion 48 and second channel wall portion 50, crossbar 60, cover 42 and screws 46 may be made of any desired composition or material such as a polymer, composite polymer, titanium, stainless steel, carbon fiber or other suitable material.

A method for fusing spinal bones together will now be described relative to FIG. 22. It should be understood that this procedure may be used during a vertebrectomy or discectomy or other neurological procedure during which it is desired to fuse spinal bones together. For ease of illustration, the embodiment will be described as used during a discectomy procedure during which the discs 18-22 (FIG. 1) are removed so that spinal bones 10-16 may be fused together. The procedure begins by situating a patient P on an operating table (not shown) and providing an appropriate incision as conventionally known to expose the spinal bones such as the bones 10-16 illustrated in the side view shown in FIG. 1 and in the anterior view illustrated in FIG. 15. (Block 70 in FIG. 22). At Block 72, the vertebrae or discs, such as discs 18-22 in FIGS. 1 and 15, are surgically removed revealing the areas 26-30 in FIGS. 2 and 16. At Block 74, the housings 32 are inserted in the direction of arrow A (FIG. 3) into the areas 26, 28 and 30 until the migration preventers 40b, 48c, 50b and 50c engage the surfaces of the spinal bones 10-16, such as the surfaces 10a and 12a illustrated in FIG. 3. (Block 74 in FIG. 22). As mentioned earlier herein, the migration preventers facilitate preventing inserting the housing 32 to a point which would cause the wall 32c to engage the spinal column S.

As illustrated in FIGS. 3 and 17, the housing 32 cooperates with adjacent spinal bones, such as bones 10 and 12 to define the graft receiving area or cavity 34 in which the graft material 38 (FIG. 4) may be inserted. As mentioned earlier herein, these graft areas 34-36 may comprise a shape which is generally rectangular, as defined by the shape of the housing 32, but it could comprise another shape by simply providing a housing 32 having a different predetermined shape. Thus, the housing 32 may be provided in a circular or arcuate shape in which case the graft area 34 would define a generally circular or arcuate area, which would cause the graft material to form a similar shape. Other curved or multi-sided shapes may be defined by providing an appropriately or correspondingly shaped housing 32, depending on the selected or desired shape that the physician would like the fused graft material 38 to assume after it has fused to the adjacent spinal bones.

At Block 76, the graft material 38 is inserted and at Block 78, the cover 42 is situated in the slot or area 52 defined by the walls 48 and 50. As mentioned earlier herein, the cover 42 facilitates covering the openings, such as openings 34a and 36a of the graft areas 34 and 36, respectively. The surgeon secures the cover 42 to one or more of the bones, as illustrated in FIGS. 5-6 and 19-20 and then closes the patient (Block 80).

Figure 24:
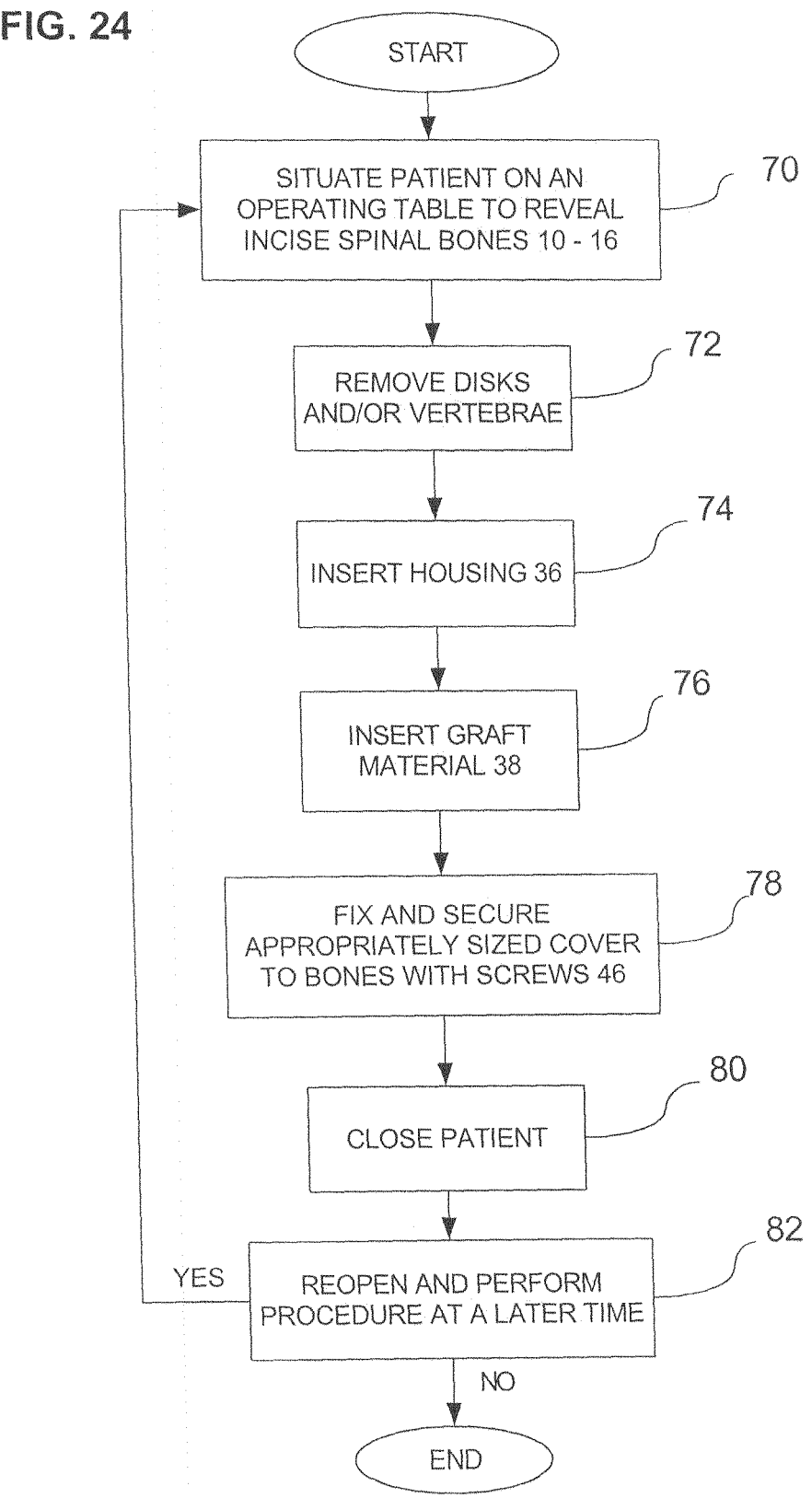
FIG. 24 is a schematic view of a process or method in accordance with an embodiment of the invention.

Again, and as mentioned earlier, a feature of the invention is that it provides a fixing system for fixing the location of the bones 12-16 relative to each other. Simultaneously, the system 24 permits the housing 32 to "float" between adjacent bones, such as bones 10 and 12 in FIGS. 3 and 6. This is advantageous for reasons mentioned earlier herein. Another advantage on this feature of the invention is that if it is necessary to operate on the same patient at a later time (Block 82 in FIG. 24) and, for example, add one or more housings 32 in order to fuse other spinal bones together, then the cover 42 can simply be removed at a later time, another discectomy or vertebrectomy performed and another housing 32 inserted. Another cover 42, or perhaps a second cover may then be used to seal the additional housing 32 after it is situated in the manner described herein. Thus, this invention provides a system and method, which is flexible and will permit the addition or insertion of additional housings 32 of the same or different sizes during a second operating procedure as illustrated in Block 82.

Figure 14:
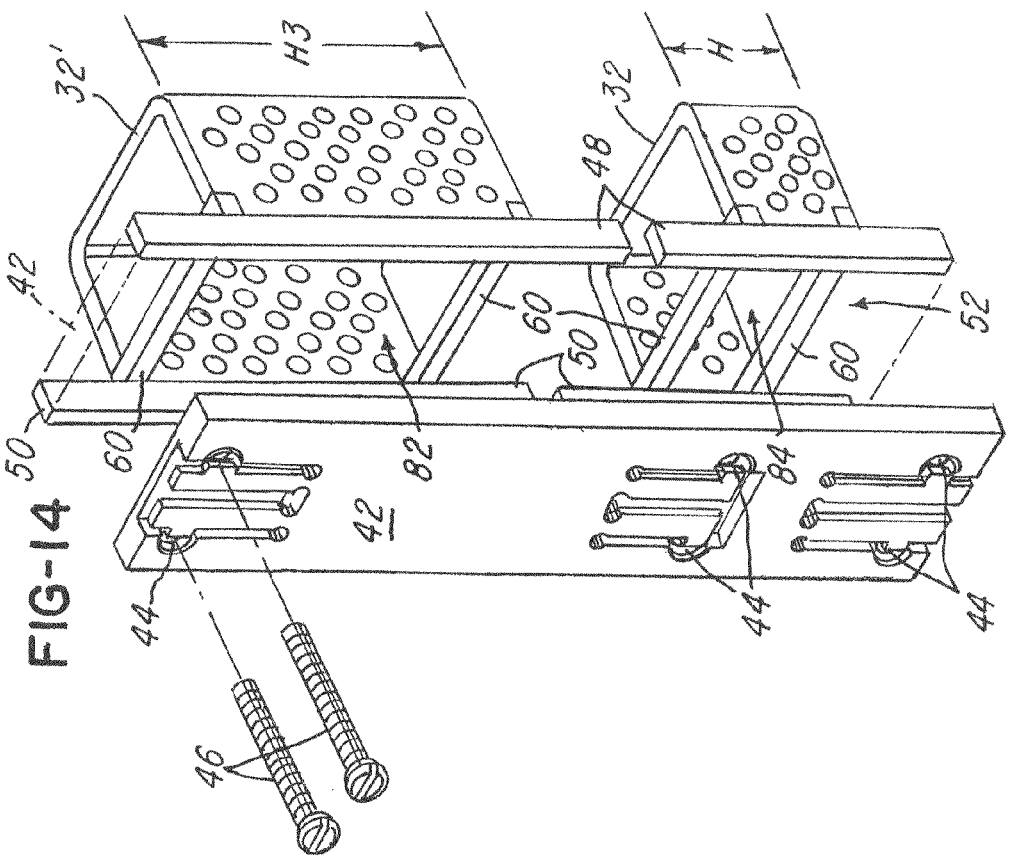
FIG. 14 is an exploded view of the housings and cover illustrated in FIG. 13.

FIGS. 1-8 and 15-20 illustrate the general procedure and use of the invention in an illustrative discectomy wherein three discs are removed, replaced with housing 32, and graft material 38 inserted as described, and cover 42 situated and mounted as described herein. In the illustration shown in FIGS. 1-8 and 15-20, three discs 18-22 are removed and the spinal bones 12-16 are fused together using the system and method as shown and described. It should be appreciated, however, that this system and method may be used with fewer or more housings 32 and with one or a plurality of covers 42 as may be desired or required. For example, if only one of the discs 18-22 needed to be excised and only two of the spinal bones 10-16 fused together, then only one housing 32 and cover 42 may be necessary. Likewise, as mentioned earlier herein, the housings 32 may comprise a different dimension or different height H (FIG. 14) to span a greater area, such as the area H4 illustrated in FIGS. 13 and 14. For example, FIGS. 13 and 14 illustrate a vertebrectomy wherein the spinal bone 12 has been removed along with the disc between spinal bones 14 and 16. This provides areas 80 and 81 in which an elongated housing 32', such as the housing 32' illustrated in FIG. 14 may be inserted. After the housings 32 and 32' are inserted between the spinal bones 10-14 and 14-16 as shown in FIG. 13, graft areas 82 and 84 are provided for receiving the graft material 38. As illustrated in FIG. 13, the cover 42 would have a corresponding elongated shape for fixing the bones 10 and 14 together and for covering both openings 82 and 84 or housings 32 and 32'.

It is also anticipated that the invention may be used in a multitude of procedures, such as a vertebrectomy (FIGS. 8 and 9), discectomy (FIGS. 1-7, 13-20, or even a combination of a vertebrectomy and discectomy as illustrated in FIGS. 13-14. As mentioned and described earlier herein, a combination of different sizes of housings 32 and covers 42 may be used as shown. Although it is preferred that a single cover 42 be used, it may be desired in some applications to use multiple covers 42, such as where the removed discs are not adjacent.

In the illustrations being described, the housings 32 comprise the crossbar 60 which cooperate with the cover 42 to prevent anterior migration of the housing after the screws 46 are secured to the spinal bones as illustrated in FIGS. 6, 9 and 13.

Figure 25:
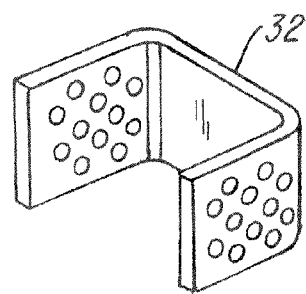
FIG. 25 illustrates another embodiment of the invention without crossbars or migration preventers.

FIGS. 25-30 illustrate other embodiments of the invention. In FIG. 25, a generally U-shaped housing 32 is provided without the walls 48 and 50 or crossbar 60. This embodiment may be useful. This may be useful if it were desired to insert housing 32 in local anatomy so that it could be loaded from the side or laterally, rather than anteriorly, as previously described.

In FIG. 26 a housing 32''' is provided with the crossbars 60, but without the walls 48 and 50. In this embodiment it may be useful to use such a housing design when the local anatomy provides limited space.

Figure 27:
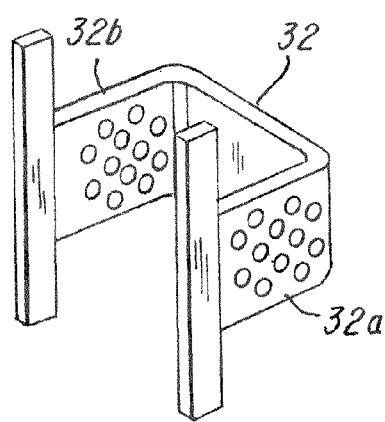
FIG. 27 is a view illustrating a plurality of migration preventers, without any crossbars.
Figure 28:
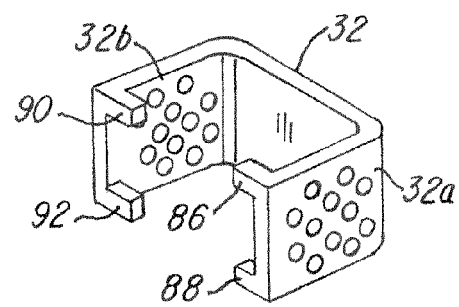
FIG. 28 is a view illustrating a housing with a plurality of projections which cooperate with the cover to prevent the housing from migrating anteriorly.

FIG. 27 illustrates yet another embodiment of the invention illustrating a housing 32 that is provided with a plurality of protrusion 86, 88, 90 and 92 that do not span completely between the walls 32b or 32a together but yet provide the protrusions 86-92 which will engage the cover 42 if the housing attempts to migrate anteriorly as described earlier herein. FIGS. 1-24, 29 and 30 show embodiments of the invention where the crossbars 60 are not integrally formed with the housing 32, but received in the notched areas 94 as shown. As mentioned earlier, the crossbars 60 may be separate or may be integrally provided with the housing 32. Providing detachable crossbars 60, such as is shown in the embodiments illustrated in FIGS. 25, 28 and 29, enable the walls 32a and 32b to flex towards and away from each other. The housing 32 may be provided with a malleable material in which case the surgeon can change the general U-shape of the housing 32 to accommodate the size or shape of the areas 34 and 36 (FIG. 17). In the embodiment described, housing 32 and cover 42 may be made of titanium, polymer or a bioresorbable material.

FIG. 31 illustrates the walls 48 and 50 having notched areas 49 and 51 for receiving the cover 42 which is dimensioned to fit, thereby eliminating the need for cross bars 60.

FIGS. 32-36 illustrate another embodiment of the invention. In this embodiment, those parts that are the same or similar to the parts illustrated in FIGS. 1-30 are identified with the same part number, except that the parts in FIGS. 31-36 have an apostrophe ("'") mark added thereto.

In this embodiment, the cage system 24 comprises a cover 400 for situating in the channel area 52 (FIG. 11) to facilitate preventing interior migration of the graft material 38. In order to secure the cover 400 over the graft area 34 or 36, a locking system, means and method are provided for retaining the cover 400 on the housing 32. In the embodiment being described, the locking system 402 comprises a plurality of screws, fastening means or fasteners 404, 406, 408 and 410 that are received in openings, such as openings 405 in the cover plate 400 as shown. Note that the fasteners 404-410 comprise a plurality of female openings or slots 404a, 406a, 408a and 410a for receiving a tool, such as a hex wrench for tightening and loosening the fasteners 404-410.

In the embodiment being described, the fasteners 404 and 408 comprise a head 404b and 408b that have a planar or flat portion 404b1 and 408b1 as shown. As best illustrated in FIGS. 34 and 35, note that the fasteners 408 and 410 each comprise threads or a threaded portion, such as threads or portions 408c and 410c of fasteners 408 and 410, respectively. Note that a distance or small radius D1 between center C1 and flat portion 408b1 in FIG. 34 is smaller than the distance or large radius D2 measured by the distance between center C1 and wall 408b2 in FIG. 35. The difference in the distances D1 and D2 facilitates defining a cam surface or lobe on the wall 408b2 whose use and purpose will be defined later herein.

In the embodiment being described, one or more of the heads 404b, 406b, 408b and 410b may comprise an indicia, such as a grind mark or other indicator 412 and 414 (FIG. 32), to facilitate and assist a user, such as a doctor, to identify the small radius portion D1 during a surgical procedure. Thus, the indicia 412 and 414 facilitate defining the surface associated with the flat portion, such as portion 404b1.

It should be understood that when the pairs of fasteners 404-406 and 408-410 are aligned such that the flat portion 404b1 and 408b1 and short or small radius portion D1 are situated in opposite or closest to wall 406b of fastener or screw 406 and wall 410b of screw 410 the adjacent fasteners 406 and 410 respectively, may be rotated and screwed into, for example, vertebrae 10, which will secure and retain the cover 400 over the graft area 34 or 36. Although not shown, the locking system of the present invention may comprise eccentric fasteners of screws having eccentric heads (i.e., where a head center is offset from a thread axis) and fasteners that are used with non-eccentric fasteners. For example, and as illustrated in FIG. 33, fasteners 404 and 408 may comprise the aforementioned eccentric, while adjacent fasteners 406 and 410, respectively, may be non-eccentric fasteners or screws.

In any event, the small radius portion D1 permits the adjacent fastener or screw such as screw 410, whether it has an eccentric or not, to be turned when the small radius portion D1 or flat portion 408b1 is situated in opposed relationship to the adjacent screw (as illustrated in FIGS. 32 and 34). For example, FIG. 34 illustrates that when the fasteners are aligned such that the indicia 414 are aligned as illustrated in FIG. 32, a gap G exists between the portions 408d1 and wall 410d of screw 410 as shown. The gap G permits either or both of the fasteners 408 and 410 to rotate in either a counterclockwise or clockwise direction during fastening and unfastening of the fasteners to the vertebrae as described earlier herein with the prior embodiments.

When it is desired to secure the cover 400 over the housing 32, the fasteners 404-408 are placed in the cover and aligned as illustrated in FIG. 32. The fasteners 404-408 are rotated and screwed into vertebrae 10 in a clockwise direction until it is seated. These fasteners 404 and 408 are then "backed out"

less than a full turn until flat portions 404b1 and 408b1 are aligned as shown in FIG. 32. The surgeon may use the indicator 412 and 414 to perform this alignment. This alignment presents the gap G (FIG. 34), which permits the fastener 410 to be rotated in a clockwise direction until completely screwed into vertebrae 10.

Next, the adjacent fastener or screw (406 for the 404-406 pair and 410 for the 408-410 pair) is inserted into opening 405 in cover 400 and in FIGS. 32 and 34 until they are fully seated into the vertebrae 10. For example, in the illustration shown in FIGS. 32 and 34, the fastener 408 is rotated in a clockwise direction with a tool, such a hex wrench (not shown) until it is fully seated into the vertebrae 10.

The fastener 408 is again rotated in the clockwise direction (as viewed) until the large radius portion D2 and the wall portion 408b2 engages and comes against the wall 410b of the fastener 410.

It should be appreciated that when the fasteners 404-410 are secured in the locked position in the manner described, they facilitate retaining themselves in the locked position. For example, if fastener 410 begins to rotate in a counterclockwise direction (as viewed in FIG. 33) it will cause fastener 408 to rotate in a clockwise direction which, in turn, causes fastener 408 to tighten and resist the counterclockwise rotation of fastener 410. If fastener 410 would rotate, fastener 408 would screw deeper into the vertebrae 10.

FIG. 36 is an illustration similar to FIG. 11 showing the orientation and alignment of the cover 400 and fasteners 404-410 to the housing 32.

Advantageously, the various embodiments of the invention illustrated in FIGS. 1-36, provide a system and method for inserting graft material 38 into a graft area 34 and 36 (FIG. 17) to fuse a plurality of bones such as bones 10-18 together. The system and method also provide means for fixing the bones 10-18 relative to each other, while permitting the housing 32 to cooperate with adjacent bones 10-18 to define a graft area 34 and 36 (FIG. 17) and to also float relative to the cover 42. The locking system illustrated in FIGS. 21-23 further facilitates providing a locking system that does not require the use of any tools, yet prevents back out of the screws 46.

Another embodiment of the invention is shown in FIGS. 37-54. Referring now to FIGS. 37-54, a spinal implant or system 110 and its various components described herein are shown. In the illustration being described, the spinal implant or system 110 is situated in an intervertebral space or disc area (not shown) between a first vertebra (not shown) and a second vertebra (not shown). In the illustration being described, the spinal implant or system 110 is used during a fusion procedure. In one illustrative embodiment, the spinal implant or system 110 comprises a cage 112, a plurality of plate elements, such as a first plate element 114 and a second plate element 116, that are slidably, movably or detachably secured to the cage 112. For ease of illustration and discussion, an exemplary embodiment will be shown and described with respect to the first and second plate elements 114 and 116, but it should be understood that more or fewer plate elements (not shown) may be used.

Note that in the embodiment being described, each of the plurality of plates elements, such as the first and second plate elements 114 and 116, and the cage 112 are adapted to permit the first and second plate elements 114 and 116 to move independently on the cage 112 in the manner described herein. In this regard, note that the first plate element 114 comprises an axis A (FIG. 39) and the second plate element 116 comprises an axis B. The first and second plate elements 114 and 116 in the illustration and the cage 112 are adapted to permit the first and second plate elements 114 and 116 to move in the direction of double arrow C and double arrow D, respectively, as illustrated in FIG. 39. In the illustration being described, the axial movement of the first and second plate elements 114 and 116 is generally perpendicular to an imaginary plane P (FIG. 39) in which the cage 112 lies. Also, note that the axis of movement of the first and second plate elements 114 and 116, along their respective axes A and B, is generally parallel with respect to each other.

Note in FIGS. 37-39 and 43 and 44A-44D, that the cage 112 is W-shaped and comprises a first leg portion 120, a second leg portion 122 and a third leg portion 124 that are generally parallel and integral or monolithic with a first wall 112a of the cage 112. Although the cage 112 is shown as being generally W-shaped, it should be understood that other shapes or configurations could be provided depending on the number of leg portions used to define the cage 112 and the number of plate elements to be inserted therein. In the illustration being described, the first wall 112a is a posterior or rear wall 126 that gets inserted first in the disc area (not shown) between the first vertebra and second vertebra. As mentioned, the first, second and third leg portions 120-124 are integrally and monolithically formed with the first wall 112a as shown.

The first leg portion 120 comprises a first side wall or surface 120a and a generally opposing bottom surface 120b; the second leg portion 122 comprises a top surface 122a and a generally opposing bottom surface 122b; and the third leg portion 124 comprises a top surface 124a and a generally opposing bottom surface 124b. In the illustration being described and as shown in FIG. 39, the top surfaces 120a, 122a and 124a and the opposing bottom surfaces 120b, 122b and 124b may be serrated, coated, treated or otherwise adapted to enhance the engagement and retention of the cage 112 with the first vertebra and the second vertebra, respectively.

Figure 44A:
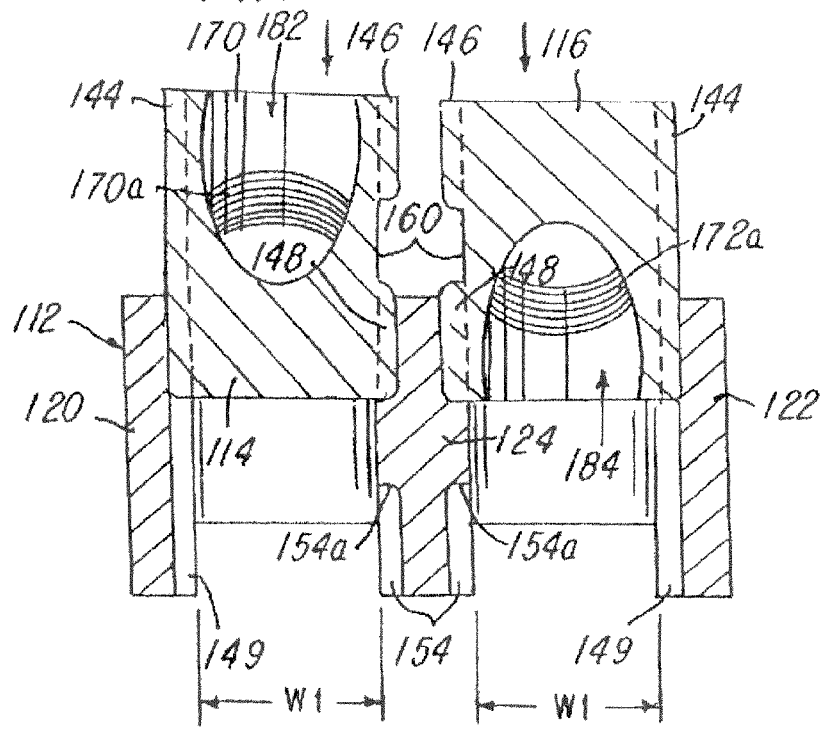
FIG. 44A is a sectional view taken along the line 44A-44A in FIG. 43.
Figure 44B:
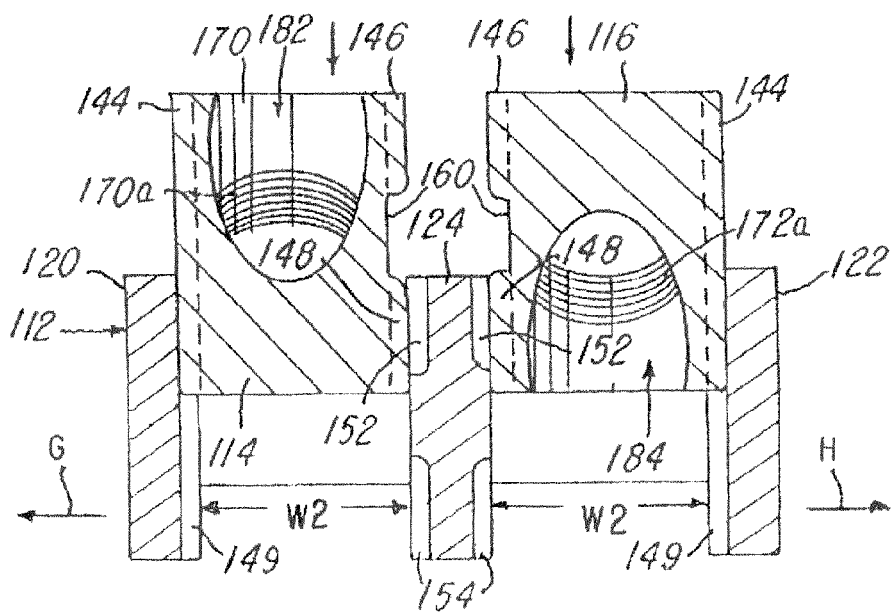
FIG. 44B is a sectional view illustrating the insertion of the plate elements into the cage.
Figure 44C:
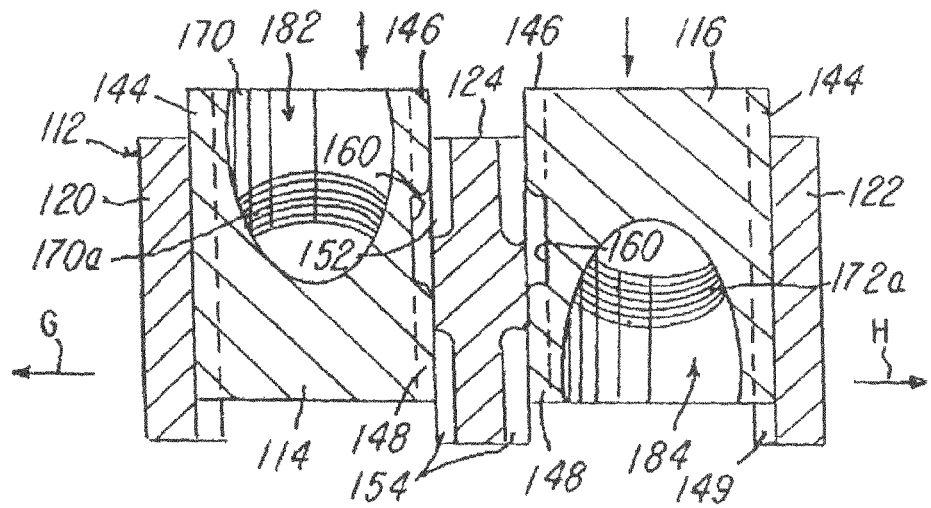
FIG. 44C is a view similar to FIG. 44B illustrating the lateral deflection (as viewed in the figure) of the leg portions.

In the illustration being described, at least one, a plurality, or all of the first, second or third leg portions 120, 122 and 124 are elastic or resilient or are otherwise adapted so that they can flex and move, for example, in the direction of arrows G and H in FIGS. 43 and 44B. For example, during the insertion of the first plate element 114 between the first leg portion 120 and third leg portion 124, as described in more detail later herein, at least one or both of the first leg portion 120 or third leg portion 124 may flex or move laterally or away from the third leg portion 124 in response to the longitudinal movement or insertion of the first and second plate elements 114 and 116 into the cage 112. This enables the first leg portion 120 and the second leg portion 122 to move in the direction of arrows G and H, respectively, (i.e., to the left and right as viewed in the FIG. 40) during insertion of the first plate element 114 and second plate element 116 into the cage 112. Of course, it should be understood that the first plate element 114 and second plate element 116 may be inserted separately or independently or could be inserted substantially simultaneously as illustrated in FIG. 40.

Referring back to FIGS. 39, 42, 43 and 44A-44D, note that the first leg portion 120 comprises a first side wall or surface 120c that is generally opposed to a second side wall or surface 124c of the third leg portion 124 as shown. The third leg portion 124 further comprises a third side wall or surface 124d that generally opposes a fourth side wall or surface 122c of the second leg portion 122. Note that the first side wall or surface 120a and second side wall or surface 124c are generally opposed to provide a first window area 130, and the third side wall or surface 124d is generally opposed to the fourth side wall or surface 122c to define and provide a second window area 132. Note that the first window area 130 receives the first plate element 114 and the second window area 132 receives the second plate element 116 as described in more detail later herein.

In the illustration being described, the first plate element 114 comprises a first plate side 114a, a second plate side 114b, a top surface 114c and a bottom surface 114d, as best illustrated in FIG. 39. Likewise, the second plate element 116 comprises a third plate side 116a, a fourth plate side 116b, a top surface 116c and a bottom surface 116d. Note that when the first plate element 114 is inserted into the first window area 130 in a manner described in more detail later herein, the first plate side 114a engages and becomes associated with the first side wall or surface 120c as illustrated in FIGS. 40-42. Likewise, when the second plate element 116 is inserted into the cage 112, the third plate side 116a becomes engaged to or associated with the second side wall or surface 122c of the second leg portion 122 and the fourth plate side 116b becomes operatively associated with or engaged to the third side wall or surface 124d of the third leg portion 124, as best illustrated in FIGS. 39, 40, 43 and 44A-44D.

Referring now to FIGS. 39-44D, the spinal implant or system 110 further comprises a lock, guide or movement controller 134 and 136 for locking the first plate element 114 and second plate element 116, respectively, to the cage 112. In the illustration being described, the cage 112 and the first and second plate elements 114 and 116 are adapted to permit controlled motion of the first and second plate elements 114 and 116 in the cage 112 and with respect to each other. Thus, the cage 112 and the first and second plate elements 114 and 116 are adapted to permit controlled motion of the first and second plate elements 114 and 116 after they are received in the cage 112. In the illustration being described, the motion is controlled motion in the axial directions of arrows C and D (FIG. 39) and along the axes A and B of the first and second plate elements 114 and 116. The locks 134 and 136 also control motion of the first and second plate elements 114 and 116 in the direction of double arrow E (FIG. 42) and double arrow F, respectively. In the illustration being described, the functions and adaptations for providing and permitting the controlled motion of the first and second plate elements 114 and 116 within the cage 112 may be separate from or combined with the locking function mentioned earlier herein. In the illustration being described, however, both the locking and controlled motion functions are incorporated in the locks, guides or movement controllers 134 and 136 which will now be described.

As mentioned earlier, the first plate side 114a of the first plate element 114 engages and becomes operatively associated and generally opposed to the first side wall or surface 120c of the first leg portion 120 and defines a first joint 140 (FIG. 40). Likewise, the second plate side 114b becomes operatively associated and generally opposed to the second side wall surface 124c of the third leg portion 124 to define a second joint 142. Similarly, the fourth plate side 116b becomes operatively associated and generally opposed to the third side wall or surface 124d to define a third joint 145, and the third plate side 116a engages and becomes associated with and generally opposed to the fourth side wall or surface 122c to define a fourth joint 147. In the illustration being described, at least one or a plurality of the pairs of joints 140, 142 and joints 145, 147 are interfitting or interlocking joints for permitting the first and second plate elements 114 and 116 to move relative to the cage 112 after the first and second plate elements 114 and 116 are mounted on or in the cage 112. In the illustration being described, the at least one or a plurality of the interfitting joints 140, 142 and 145, 147 both retain and lock the first and second plate elements 114 and 116 in the cage 112 and also are adapted to permit the controlled motion of the first and second plate elements 114 and 116 in the directions of double arrows C and D (FIG. 39) and double arrows E and F (FIG. 42). Thus, note that the at least one or a plurality of the interfitting joints 140, 142 and 145, 147 permit, for example, sliding movement of each of the first and second plate elements 114 and 116 and on the cage 112. In one embodiment, the sliding movement of each of the first and second plate elements 114 and 116 is axial or longitudinal movement in their respective axes A and B, as illustrated in FIGS. 39 and 40. Note that the sliding movement is generally parallel to an axis CA (FIGS. 40 and 41) of the cage 112.

Referring now to FIGS. 47A-47B, details of the locks, guides or movement controllers 134 and 136 will now be described. For ease of illustration and description, the first plate element 114 will be described, with it being understood that the second plate element 116 is constructed substantially identically, but is situated in the cage 112 in a opposite orientation (i.e., upside down relative to the first plate element 114 in FIG. 39) when it is inserted in the cage 112.

The first plate element 114 comprises a first elongated rail, boss or projection 144 that projects or extends from the first plate side 114a and is received in a complementary mating receiving area, groove, channel, slot or notch 149 (FIGS. 43-44D) in the first side wall or surface 120c of the first leg portion 120 when the first plate element 114 is slidably received between the first and third leg portions 120 and 124. The second plate side 114b comprises a first rail, boss or projection 146 and a second rail, boss or projection 148 as shown. Note that these projections lie in a common plane P1 (FIG. 45) and have a common axis.

The first rail, boss or projection 146 comprises an end or step 146a and the second rail, boss or projection 148 comprises an end or step 148a. The ends or steps 146a and 148a cooperate to define a receiving area, groove, channel, slot or notch 150 (FIG. 46) for receiving a mating portion or intermediate area 160 whose function will be described later herein. Note that when the first plate element 114 is slidably received between the first and third leg portions 120 and 124, the first rail, boss or projection 146 and the second rail, boss or projection 148 are received in the grooves, channels, slots or notches 152 and 154, respectively, as best illustrated in FIG. 44A. As best illustrated in FIG. 40, the first and second plate elements 114 and 116 may be guided or inserted into the cage 112 from the top or bottom, such as in the direction of arrow X (FIG. 40), or from a bottom or in the direction of arrow Y.

Figure 44D:
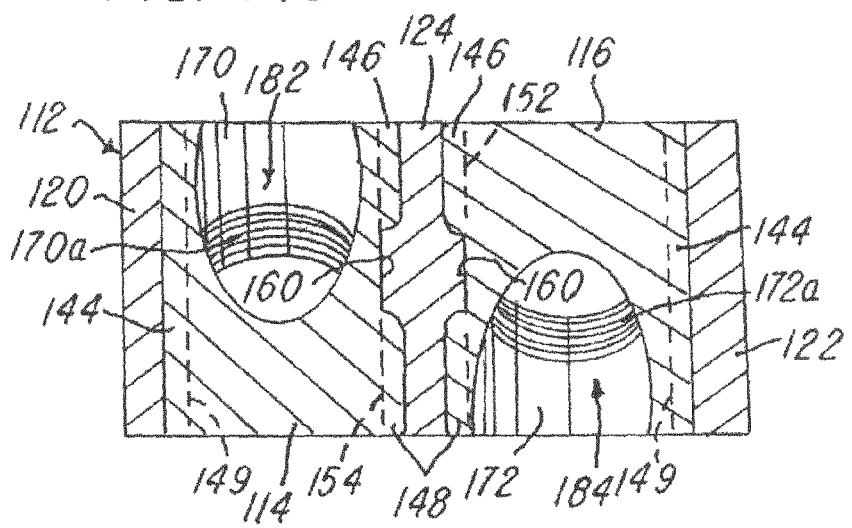
FIG. 44D is a sectional view taken along the line 44D-44D in FIG. 42 after the plate elements are locked in the cage.

As alluded to earlier herein, as the first and second plate elements 114 and 116 are inserted into the cage 112, the rails, bosses or projections 144, 146 and 148 mate with and are received in their respective groove, channel, slot or notch 149, 152 and 154, respectively. Note that the rails, bosses or projections 144, 146 and 148 have a cross-sectional radius or curvature that complements the shape of the grooves, channels, slots or notches 149, 152 and 154. The ends 152a and 154a (FIG. 43) also have a radius that mates with the ends 152a and 154a of the grooves, channels, slots or notches 152 and 154. As best illustrated in FIGS. 39 and 44B, an intermediate area 60 exists between the groove, channel, slot or notch 152 and 154 and becomes situated between the rails, bosses or projections 146 and 148 to retain or lock the first plate element 114 in the cage 112. During insertion of the first plate element 114 into the cage 112 (assuming a top insertion as shown in FIGS. 39 and 40), the rail, boss or projection 148 is inserted into the groove, channel, slot or notch 152 (best seen in FIGS. 39, 43 and 44A) and rail, boss or projection 144 is received in the rail receiving area, groove, channel, slot or notch 149 and the first plate element 114 is moved downwardly in the direction of arrow X (FIG. 40) until an end 148b (FIG. 46) of the first plate element 114 engages the end 152a of the groove, channel, slot or notch 152. The end 148a is slightly chamfered or angled when further downward force is applied, the first plate element 114 exerts a lateral force (as viewed in FIG. 40) to cause the elastic or resilient first leg portion 120 to move or be deflected in the direction of arrow G (FIGS. 44B-44D) until the rails, bosses or projections 146 and 148 are received in their respective grooves, channels, slots or notches 152 and 154, respectively as shown in FIG. 44D. Notice in FIG. 44A a width between leg portions 122 and 124 is width W1, as opposed to a width W2 which is larger than W1 (FIGS. 44B and 44C) when the rail, boss or projection 148 engages and slides over the intermediate area 160. This causes the leg portions 120 and 124 to deflect outwardly as mentioned herein. Thus, the rail, boss or projection slides over the intermediate area 60 until the rails, bosses or projections 146 and 148 are received in their respective grooves, channels, slots or notches 152 and 154.

Likewise, if one or more of the first or second plate elements 114 or 116 are inserted, for example, from a bottom of the cage 112 (as viewed in FIG. 44A), then its respective rails, bosses or projections 144 and 146 engages an end 154a (FIG. 44A) of the groove, channel, slot or notch 154 so that, for example, when the second plate element 116 is driven in the direction of arrow Y (FIG. 40) and further into the cage 112, the movement causes the second leg portion 122 to deflect in the direction of arrow H (FIG. 44B). This enables the rail, boss or projection 146 to slide over the intermediate area 160 until the rails, bosses or projections 146 and 148 are received in the grooves, channels, slots or notches 152 and 154, respectively. Again, the second leg portion 122 is elastic and resilient so that as the second plate element 116 is driven into the cage 112, it is deflected or moves laterally in the direction of arrow G (FIGS. 44B-44D) until the rails, bosses or projections 146 and 148 are received in their respective grooves, channels, slots or notches 152 and 154, respectively.

Figure 45:
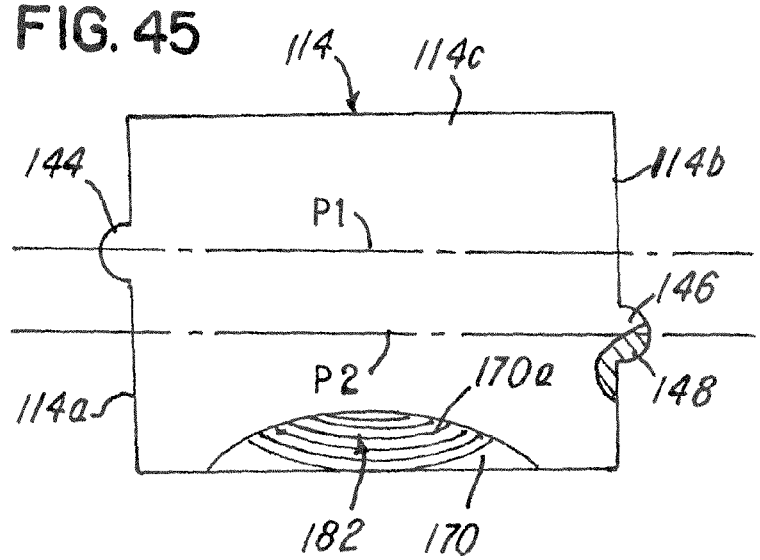
FIG. 45 is a plan view of one of the sliding plate elements.
Figure 46:
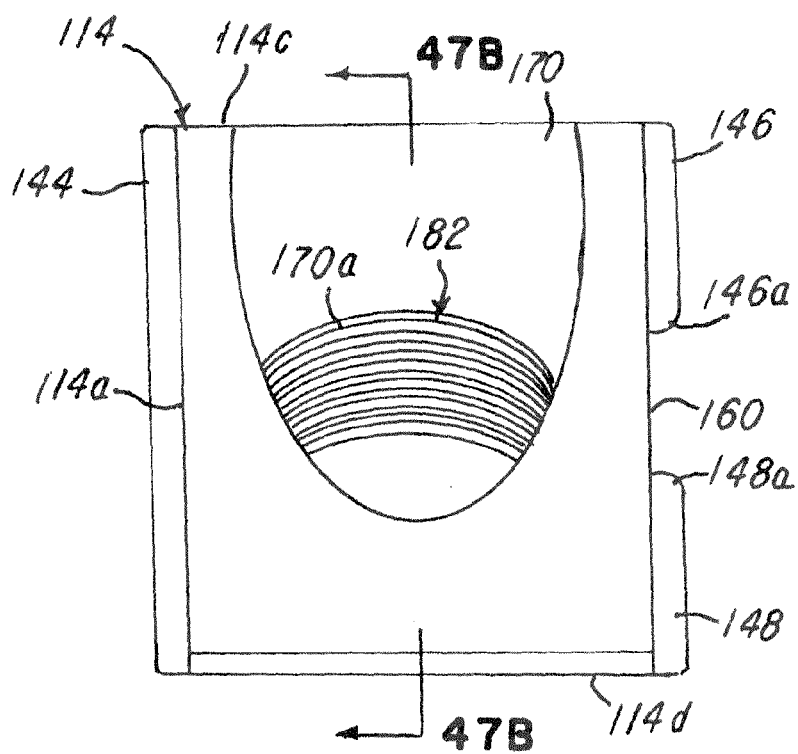
FIG. 46 is a front view of the plate element shown in FIG. 45.
Figure 50:
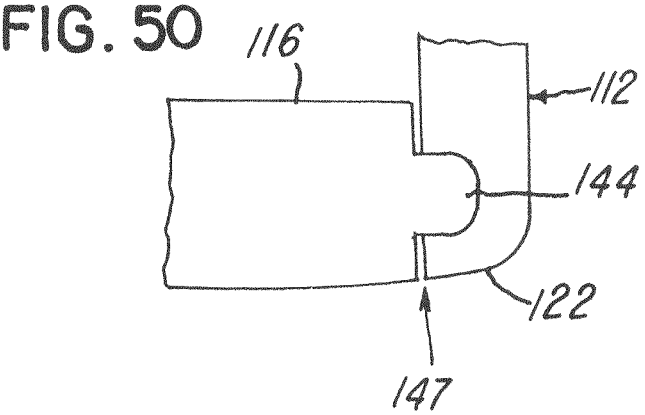
FIGS. 50-52 illustrate various interconnecting joints that may be used in the illustrating being described.
Figure 51:
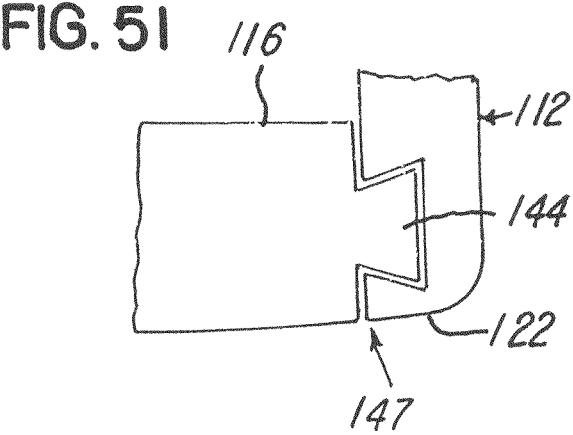

Note in FIG. 45 that the rails, bosses or projections 146 and 148 each have a longitudinal axis that lies in the plane (P1), and the rail, boss or projection 144 lies in plane (P2). Note that these planes P1 and P2 are offset and are parallel as shown. The rails, bosses or projections 146 and 148 are offset from the rail, boss or projection 144.

Figure 52:
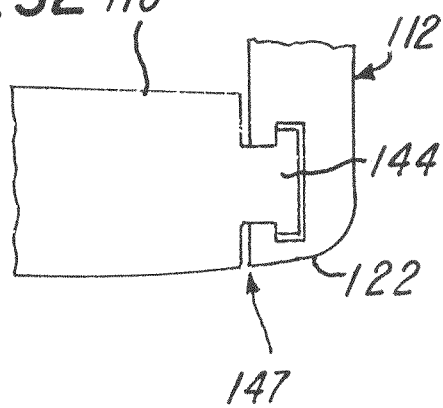

Advantageously, the joints 140, 142, 145 and 147 at or near the intersection of the first and second plate elements 114 and 116 and the various side walls or surfaces 120c, 122c and 124c are adapted to provide both locking of the first and second plate elements 114 and 116 in the cage 112 and also permit controlled motion of the first and second plate elements 114 and 116 in the cage 112. The controlled motion in the illustration being described is an axial, sliding motion, but it is contemplated that other types of motions and in different directions could be provided and controlled as well. For example, the joints 140, 142, 145 and 147 could be configured to enable the first and second plate elements 114 and 116 to be inserted into the cage 112 in different ways, such as from an anterior, top, bottom or front direction of the cage 112 as shown earlier herein relative to the other embodiments. It is also contemplated that the one or more of the joints 140, 142 and joints 145, 147 could comprise different characteristics such as a dovetail (FIG. 51) or a T-shaped boss and groove (FIG. 52). Alternatively, they could comprise the rail and groove illustrated in FIGS. 37-47B and 50 as described earlier herein. In the illustration being described, the rails, bosses or projections 146 and 148 could be viewed as a common boss or projection but interrupted. One feature of the embodiment being described is that the cage 112 comprises the grooves, channels, slots or notches 150, 152 and 154 that are arranged and adapted to complement the location and shapes of the rails, bosses or projections 144, 146 and 148, respectively, so that the first and second plate elements 114 an 116 fit snugly and become securely captured, fastened or locked in the cage 112 after they are received in the home position shown in FIG. 41.

Although it is shown as the first and second plate elements 114 and 116 comprising the rails, bosses or projections 144, 146 and 148 with the cage 112 comprising the complementary-shaped grooves, the cage 112 could comprise the bosses or projections with the first and second plate elements 114 and 116 comprising the grooves. Alternatively, one or more of the bosses or projection in complementary grooves could be arranged, for example, so that some of the bosses or projections are arranged on the cage 112 and their mating grooves or channels arranged on the first or second plate elements 114 or 116 and some of the bosses or projections arranged on the first or second plate elements 114 and 116 with their mating grooves or channels in the cage 112.

Another advantageous feature of the embodiments being described is that the spinal implant or system 110 comprises means for securing the cage 112 in the intervertebral space or area (not shown) between the first and second vertebra. In the illustration being described, each of the first and second plate elements 114 and 116 comprise internal walls 170 and 172 (FIG. 40), respectively, each having female threaded areas or portions 170a and 172a that receive a screw 178 having mating male threads 180 (FIG. 49). This is illustrated in FIG. 47B. Again, as mentioned earlier, the first and second plate elements 114 and 116 are generally mirror images of each other, except that they are upside down with respect to each other as shown.

Notice in FIG. 47B that the wall 170 defines an aperture 182 and wall 172 (FIG. 44D) defines aperture 184 for receiving and guiding the screw 178 along a desired axis, such as axis SA, as the screw 178 travels through the first plate element 114 at a predetermined angle PA1 as best illustrated in FIGS. 47 and 48. Thus, the aperture 182 guides and directs the screw 178 to traverse through the first plate element 114 at the predetermined angle PA1 with respect to the cage 112. In the illustration being described, this predetermined angle PA1 is on the order of about 30-80 degrees. The aperture 184 guides the screw 178 in a second predetermined angle PA2.

Figure 37:
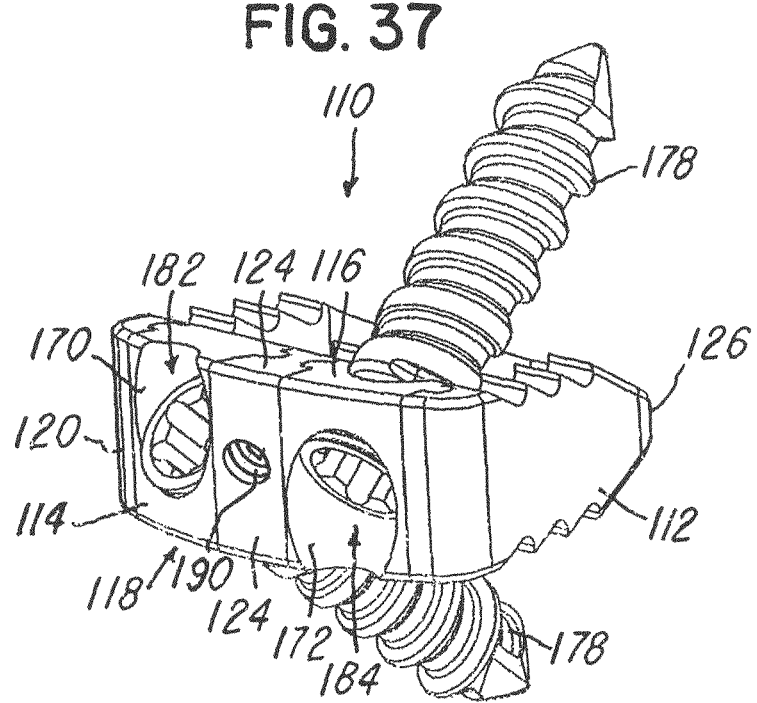
FIG. 37 is a perspective view of another embodiment of the invention.
Figure 38:
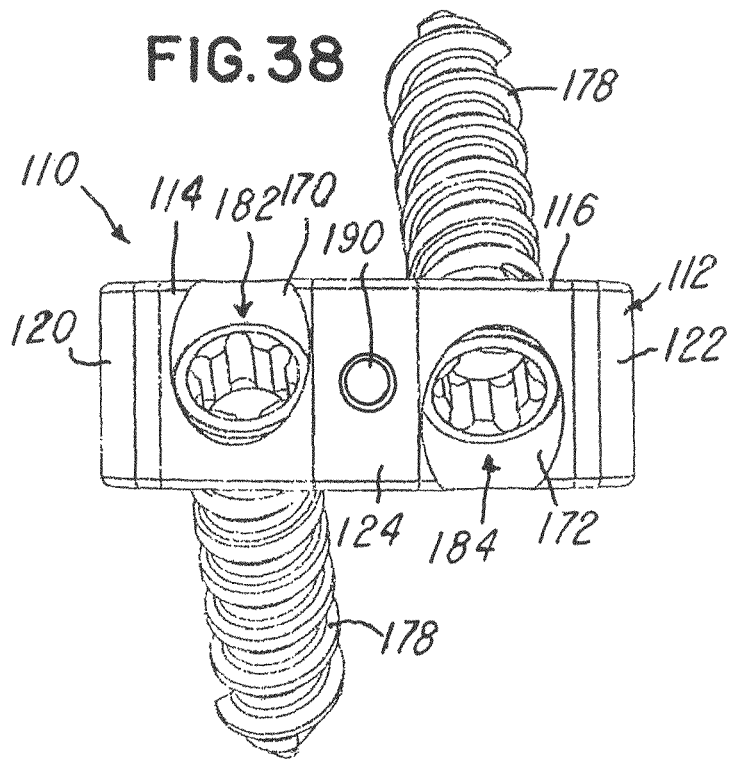
FIG. 38 is a front view of the embodiment shown in FIG. 37.

Notice that once the first and second plate elements 114 and 116 are situated in the cage 112 as illustrated in FIGS. 41 and 42 and the cage 112 threadably receives the screws 178 they become automatically positioned and oriented at the predetermined angle PA1 and a second predetermined angle PA2, as illustrated in FIGS. 37, 38 and 48. It is contemplated that the first and second predetermined angles PA1 and PA2 (FIG. 48) could be the same as illustrated in FIGS. 37, 38 and 48, but they could be different. For example, the first predetermined angle PA1 of the first plate element 114 that causes the screw 178 to traverse through the cage 112 could be less than or greater than the second predetermined angle PA2 of the second plate element 116 that causes the screw 178 to traverse through the cage 112, and vice versa.

Advantageously, the first and second plate elements 114 and 116 may be provided in a kit (not shown) with a plurality of the first and second plate elements 114 and 116 (not shown) having apertures 182 and 184 that define different predetermined angles PA1 and PA2 so that a person, such as a surgeon, can select and adapt the spinal implant or system 110 in response to the morphological characteristics of the patient.

Notice also that the placement and arrangement of the first and second plate elements 114 and 116 in the cage 112 causes the axes of their respective apertures 182 and 184 to diverge as illustrated in FIGS. 37, 38 and 48.

As best illustrated in FIG. 47B, means or a screw lock for locking the screw 178 that is received in its respective aperture 182 or 184 is provided. In the illustration being described, the lock comprises a finely-threaded male threads 180 that is tapered as illustrated in FIG. 49. As illustrated in FIGS. 41, 44B-44D and 47B, each of the threads 170a and 170b in the first and second plate elements 114 and 116, respectively, comprise a corresponding taper so that after the screws 178 are received in each of the apertures 182 and 184 and screwed into bone, the threads 180 of the screws 178 mate with and become locked in the threads 170a and 170b. Given that the first and second plate elements 114 and 116 are mounted in the cage 112 and the screws 178 screwed into bone, the cage 112, therefore, becomes locked and securely mounted in the intervertebral space between the first and second vertebrae.

Figure 53:
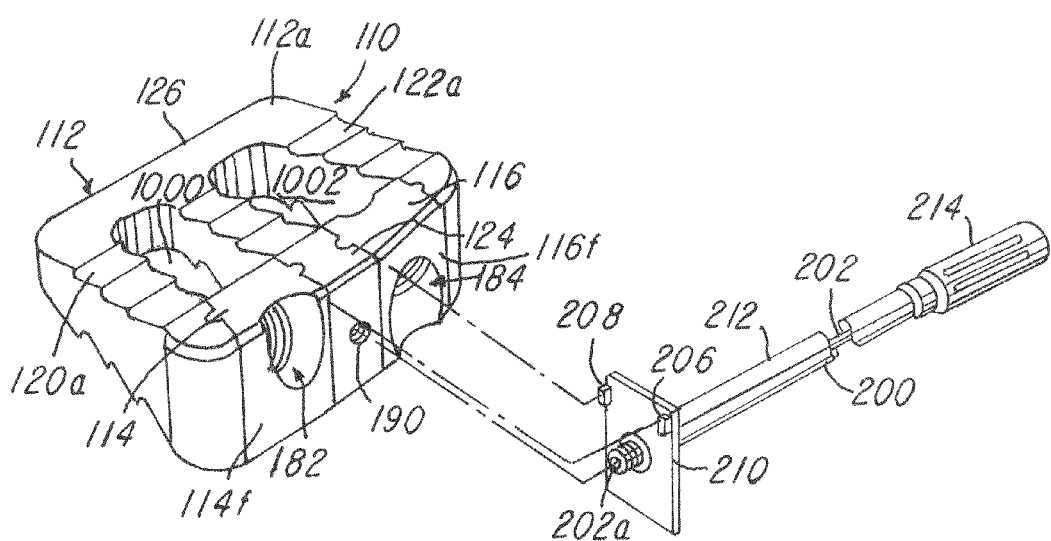
FIG. 53 is a view of a tool that locks the plates to the cage during insertion and without obstructing access to any aperture in the plate.

In the illustration being described, the cage 112 comprises a wall 190 (FIG. 41) that defines a threaded tool receiving aperture 190a for receiving a threaded tool 200 (FIGS. 53 and 54) to facilitate placement of the cage 112 between the first and second vertebrae. In one embodiment, the tool 200 may have a mechanism or means to lock the first and second plate elements 114 and 116 in the cage 112 during the implant insertion process. FIGS. 53 and 54 show the tool 200 having an internal rod 202 having a threaded end 202a for threadably engaging the threaded aperture 190a.

The tool 200 also has a pair of spaced engaging members 206, 208 for engaging the plates 114 and 116, respectively, during the insertion process. The engaging members 204 and 206 could have serrations (not shown) and be integrally formed in the support 210 that is secured to a handle 212. The engaging members 206 and 208 could be a polymer, such as rubber or plastic. Alternatively, they could be male projections that are received in female openings (not shown) in the face or front surfaces 114f, 116f of the plates 114 and 116, respectively.

Advantageously, the tool 200 holds the plates 114 and 116 in place in the cage 112 during insertion of the cage 112 in the patient. The tool support 210 overlaps the faces 114f and 116f only enough so that the projections 106, 108 can engage them. The support 210 does not interfere with access to the apertures 182, 184. Thus, the screws 178 can be inserted into the apertures 182 and 184 and screwed into bone after cage 112 placement and while the tool 200 is mounted on the cage 112. Thus, the tool 200 does not interfere with the insertion of the screws 178. Note that the pressure that the engaging members 206, 208 engage or apply to plates 114 and 116, respectively, can be changed by rotating the handle 214 that is coupled to the threaded end 202a, thereby enabling the position of plates 114 and 116 to be changed if desired while they are locked in the cage 112.

As mentioned earlier and as shown, the cage 112 is W-shaped. As illustrated in FIGS. 42 and 43, the first side wall or surface 120c, second side wall or surface 124c and wall or surface 112a1 of the cage 112 cooperate to define a generally U-shaped graft-receiving area 1000. Likewise, the fourth side wall or surface 122c of the second leg portion 122 and the third side wall or surface 124d and the wall or surface 112a2 of the cage 112 define a second graft-receiving area 1002. Thus, the cage 112 in the illustration being described has a plurality of graft-receiving areas 1000 and 1002 that are divided by the third leg portion 124 in the illustration being shown. It should be understood that more or fewer graft receiving areas could be provided depending upon the configuration of the cage 112.

During use, the first and second plate elements 114 and 116 may be arranged in the cage 112 as illustrated in FIGS. 41 and 42 and graft material (not shown) inserted and packed into the graft receiving areas 1000 and 1002. Alternatively, the cage 112 may be inserted into the intervertebral space between the first and second vertebrae and packed in-situ. In this regard, the first and second window areas 130 and 132 open into the graft-receiving areas 1000 and 1002, respectively, and enable the surgeon to place graft material in-situ during a surgical procedure. This is accomplished by insertion of the cage 112 and packing or graft material through the window areas 130 and 132 and into the graft-receiving areas 1000 and 1002, respectively. Thereafter, the first and second plate elements 114 and 116 are slidably mounted in the cage 112.

Alternatively, the first and second plate elements 114 and 116 are situated in the cage 112 and the screw apertures 182 and 184 used for packing graft material in the graft-receiving areas 1000 and 1002. The screws 178 are inserted into the apertures 182 and 184 of the first and second plate elements 114 and 116, respectively, and then screwed into the first and second vertebrae. Also, the first and second plate elements 114 and 116 could have different sizes, such as different heights, widths or thicknesses (not shown), along the windows 130 and 132 which could also have different widths.

Also, although the first and second plate elements 114 and 116 are shown such that they are positioned in the cage 112 at an interior or front area 118 of the cage 112, it should be understood that they could be situated in one or more of the other surfaces or walls of the cage 112, such as in the side walls.

Advantageously, the first and second plate members 114 and 116 can "float" by moving vertically independent of the cage body and, importantly, independently of each other. This serves to decouple the axial forces between the cage 112 and first and second plate members 114 and 116. The tool 200 or insertion instrument may have the capability to contact or engage the first and second plate members 114 and 116 so that they do not move during the implant insertion process because deployment of the first and second plate members 114 and 116 during insertion may be undesirable.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A spinal implant comprising:
a cage having a plurality of windows; and
a plurality of plate elements, each of said plurality of plate elements having an aperture for receiving a screw;
said plurality of plate elements and said cage being adapted to permit said plurality of plate elements to move independently on said cage;
wherein said cage and said plurality of plate elements are adapted to permit controlled motion of said plurality of plate elements in said cage:
wherein said controlled motion is axial, sliding motion of said plurality of plate elements in said cage;
wherein said plurality of plate elements comprise a first plate comprising a first side and a second side and a second plate having a third side and a fourth side, said cage comprising a first cage surface and a generally opposed second cage surface that cooperate to define a first cage window, said cage further comprising a third cage surface and a fourth cage surface that cooperate to define a second cage window, said first and second plates being received in said first and second cage windows, respectively.

2. The spinal implant as recited in claim 1 wherein said plurality of plate elements each have an axis of movement that is generally parallel.

3. The spinal implant as recited in claim 1 wherein each of said plurality of plate elements have an axis of movement that is generally perpendicular to a plane of said cage.

4. The spinal implant as recited in claim 1 wherein each of said plurality of plate elements move with respect to said cage along an axis that is generally perpendicular to a plane of said cage.

5. The spinal implant as recited in claim 1 wherein each of said plurality of plate elements comprises a wall that defines said aperture, said aperture causing said screw to traverse each of said plurality of plate elements at a predetermined angle with respect to said cage.

6. The spinal implant as recited in claim 5 wherein said predetermined angle is between 30-80 degrees.

7. The spinal implant as recited in claim 1 wherein said plurality of plate elements comprises a first plate and a second plate that are slidably received on said cage, said first plate having a first wall that defines a first aperture having a first aperture axis and said second plate having a second wall that defines a second aperture having a second aperture axis, said first and second apertures receiving a first screw and a second screw, respectively; said first and second screws traversing said first and second plates at a first predetermined angle and a second predetermined angle, respectively.

8. The spinal implant as recited in claim 7 wherein each of said first and second predetermined angles is a fixed angle trajectory that falls between 30-80 degrees.

9. The spinal implant as recited in claim 7 wherein said first and second aperture axes diverge so that said first screw can be screwed into a first vertebrae and said second screw can be screwed into a second vertebrae after said cage is received between said first and second vertebrae.

10. The spinal implant as recited in claim 1 wherein said each of said screws that are received in said plurality of plate elements comprises a lock for locking into said plurality of plate elements.

11. The spinal implant as recited in claim 7 wherein each of said first and second screws that are received in said first plate and said second plate, respectively, comprises a lock for locking into said plurality of plate elements.

12. The spinal implant as recited in claim 11 wherein said lock is a tapered thread.

13. The spinal implant as recited in claim 7 wherein said first wall comprises a first female thread and said second wall comprises a second female thread, each of said first screw and said second screw comprising a tapered male thread for mating with said first and second female threads.

14. The spinal implant as recited in claim 1 wherein said first side and said second side of said first plate cooperates with said first cage surface and said second cage surface, respectively, to define a first joint and a second joint; said third side and said fourth side of said second plate cooperate with said third cage surface and said fourth cage surface, respectively, to define a third joint and a fourth joint.

15. The spinal implant as recited in claim 14 wherein the first joint, second joint, third joint and fourth joint are adapted to retain said first plate and said second plate in said cage and also permit relative movement of said first and second plates and said cage.

16. The spinal implant as recited in claim 15 wherein said first joint, second joint, third joint and fourth joint comprise at least one of a rail and groove joint, a dovetail joint, a groove and an interrupted boss, notch or projection.

17. The spinal implant as recited in claim 15 wherein each of said first side and said first cage surface comprises at least one of a first projection or a first groove and each of said second side and said second cage surface comprises at least one of a complementary second groove or a complementary second projection, respectively, that mates with and receives said first projection or said first groove, respectively.

18. The spinal implant as recited in claim 17 wherein each of said third side and said fourth side comprises at least one of a third projection or a third groove and each of said third cage surface and said fourth cage surface comprises at least one of a complementary second groove or a complementary second projection, respectively, that mates with and receives said third projection or said third groove, respectively.

19. A spinal implant comprising:
a cage having a plurality of windows; and
a plurality of plate elements, each of said plurality of plate elements having an aperture for receiving a screw;
said plurality of plate elements and said cage being adapted to permit said plurality of plate elements to move independently on said cage;
wherein each of said plurality of plate elements comprises a plate lock for locking a first and a second plate onto said cage;
wherein said plate lock comprises a notch and a mating boss.

20. The spinal implant as recited in claim 19 wherein said plurality of plate elements comprises a first plate and a second plate comprising said notch and said cage comprises said mating boss.

21. The spinal implant as recited in claim 1 wherein said cage is generally W-shaped.

22. The spinal implant as recited in claim 21 wherein said cage comprises a first leg portion, a second leg portion, a third leg portion and a joining portion joining said first, second and third leg portions.

23. The spinal implant as recited in claim 22 wherein at least said first and second leg portions are at least one of elastic or resilient so that they can move away from said third leg portion when a first plate and a second plate, respectively, are mounted on said cage.

24. The spinal implant as recited in claim 1 wherein each of said plurality of plate elements and said cage have an interfitting joint for permitting said plurality of plate elements to move relative to said cage after said plurality of plate elements are mounted on said cage, said interfitting joint also retaining said plurality of plate elements on said cage.

25. A spinal implant comprising:
a cage having a plurality of windows; and
a plurality of plate elements, each of said plurality of plate elements having an aperture for receiving a screw;
said plurality of plate elements and said cage being adapted to permit said plurality of plate elements to move independently on said cage;
wherein each of said plurality of plate elements and said cage have an interfitting joint for permitting said plurality of plate elements to move relative to said cage after said plurality of plate elements are mounted on said cage, said interfitting joint also retaining said plurality of plate elements on said cage;
wherein said interfitting joint permits sliding movement of each of said plurality of plate elements on said cage.

26. The spinal implant as recited in claim 25 wherein said sliding movement of each of said plurality of plate elements is along its longitudinal axis.

27. The spinal implant as recited in claim 26 wherein said sliding movement is generally parallel to an axis of said cage.

28. The spinal implant as recited in claim 25 wherein said spinal implant comprises a tool having a lock for locking said plates in said cage during insertion of said cage in a patient.

29. The spinal implant as recited in claim 28 wherein lock is a plurality of projections that prevent said plates from moving in said cage during such insertion.

30. A spinal implant comprising;
a cage;
a first plate; and
a second plate;
said cage, said first plate and said second plate having a plurality of interfitting joints for permitting said first and second plates to move relative to said cage after said first and second plates are mounted on said cage and a lock or retainer for locking or retaining, respectively, said first and second plates on said cage after they are mounted thereto:
wherein said plurality of interfitting joints permit sliding movement of each of said first plate and said second plate on said cage.

31. The spinal implant as recited in claim 30 wherein said sliding movement of each of said first and second plates is along its longitudinal axis.

32. The spinal implant as recited in claim 31 wherein said sliding movement is generally parallel to an axis of said cage.

33. The spinal implant as recited in claim 30 wherein said cage is generally W-shaped.

34. The spinal implant as recited in claim 33 wherein said cage comprises a first leg portion, a second leg portion, a third leg portion and a joining portion joining said first, second and third leg portions.

35. The spinal implant as recited in claim 34 wherein at least said first and second leg portion are at least one of elastic or resilient and move in response to said first plate and second plate being mounted on said cage.

36. The spinal implant as recited in claim 34 wherein said first leg portion has a first surface, said third leg portion has a second surface and a third surface, said second leg portion has a fourth surface, said first and second surfaces and said third and fourth surfaces being generally opposed to provide a first window area for receiving said first plate and a second window area for receiving said second plate.

37. The spinal implant as recited in claim 36 wherein said first plate comprises a first side and a second side that become associated with said first surface and said second surface, respectively, of said cage when said first plate is mounted in said cage, said second plate comprises a third side and a fourth side that become associated with said third surface and said fourth surface, respectively, of said cage when said second plate is mounted in said cage.

38. The spinal implant as recited in claim 37 wherein said first side and said first surface cooperates to define a first interfitting joint, said second side and said second surface cooperate to define a second interfitting joint, said third side and said third surface cooperate to define a third interfitting joint and said fourth side and said fourth surface cooperate to define a fourth interfitting joint.

39. The spinal implant as recited in claim 38 wherein at least one of said first, second, third or fourth interfitting joints is not the same as the others.

40. The spinal implant as recited in claim 38 wherein a plurality of said first, second, third and fourth interfitting joints are the same.

41. The spinal implant as recited in claim 38 wherein said first and third interfitting joints are the same.

42. The spinal implant as recited in claim 38 wherein said second and fourth interfitting joints are the same.

43. The spinal implant as recited in claim 38 wherein at least one of said first interfitting joint and said second interfitting joint, and at least one of said third interfitting joint and said fourth interfitting joint are adapted to retain said first plate and said second plate in said cage and also permit movement of said first and second plates on said cage.

44. The spinal implant as recited in claim 38 wherein said first interfitting joint, said second interfitting joint, said third interfitting joint and said fourth interfitting joint each comprise a projection or boss and complementary mating groove or notch.

45. The spinal implant as recited in claim 44 wherein said projection or boss is elongated and interrupted.

46. The spinal implant as recited in claim 37 wherein each of said first side and said third side at least one of a first projection or a first groove and each of said first surface and said second surface comprising at least one of a second groove or a second projection that mates with and receives said first projection or said first groove, respectively.

47. The spinal implant as recited in claim 30 wherein spinal implant comprises a plate lock for locking said first and second plates onto said cage.

48. The spinal implant as recited in claim 47 wherein said lock is defined by comprises a notch or groove and a mating boss or projection at a joint between at least one surface of said first plate and said second plate and said cage.

49. The spinal implant as recited in claim 48 wherein each of said first and second plates comprises said notch and said cage comprises said mating boss.

50. The spinal implant as recited in claim 30 wherein said first and second plates each have an axis of movement that is generally parallel.

51. The spinal implant as recited in claim 30 wherein each of said first and second plates each have an axis of movement that is generally perpendicular to a plane of said cage.

52. The spinal implant as recited in claim 30 wherein each of said first and second plates are slidably mounted on said cage and move with respect to said cage along an axis that is generally perpendicular to a plane of said cage.

53. The spinal implant as recited in claim 30 wherein each of said first and second plates comprise a wall that defines an aperture, said aperture causing each screw in said first and second plates to traverse through said first and second plates at a predetermined angle with respect to said cage.

54. The spinal implant as recited in claim 53 wherein said predetermined angle is between 30-80 degrees.

55. The spinal implant as recited in claim 30 wherein said first and second plates are slidably received on said cage, said first plate having a first wall that defines a first aperture having a first aperture axis and said second plate having a second wall that defines a second aperture having a second aperture axis, said first and second apertures receiving a first screw and a second screw, respectively, said first and second screws traversing through said first and second plates at a first predetermined angle and a second predetermined angle.

56. The spinal implant as recited in claim 55 wherein said first and second predetermined angles is a fixed angle trajectory that falls between 30-80 degrees.

57. The spinal implant as recited in claim 55 wherein said first and second aperture axes diverge so that said first screw can be guided and screwed in a first vertebrae and said second screw can be screwed into a second vertebrae after said cage is received between said first and second vertebrae.

58. The spinal implant as recited in claim 30 wherein said each screw that is received in said first and second plates comprises a lock for locking into said first and second plates.

59. The spinal implant as recited in claim 30 wherein each screw that is received in said first and second plates comprises a lock for locking into said first and second plates.

60. The spinal implant as recited in claim 59 wherein said lock is a tapered thread.

61. The spinal implant as recited in claim 55 wherein said first wall comprises a first female thread and said second wall comprises a second female thread, each of said first screw and said second screw comprising a tapered male thread for mating with said first and second female threads.

62. The spinal implant as recited in claim 30 wherein said cage and said first and second plates are adapted to permit controlled motion of said first and second plates in said cage.

63. The spinal implant as recited in claim 62 wherein said controlled motion is an axial, sliding motion of said first and second plates in said cage.

64. The spinal implant as recited in claim 30 wherein said spinal implant comprises a tool having a lock for locking said plates in said cage during insertion of said cage in a patient.

65. The spinal implant as recited in claim 64 wherein lock is a plurality of projections that prevent said plates from moving in said cage during such insertion.

66. An apparatus for surgical use in humans, comprising:
 a housing for insertion between vertebrae in a human spine;
 a recess in said housing for receiving bone graft material;
 a cover securable to at least one of the adjacent vertebrae and being configured to block egress of the bone graft material from said recess;
 said cover and said housing being slidably engaged one to the other; and
 said cover comprising a first plate and a second plate having a plurality of interfitting joints for permitting said first and second plates to move relative to said housing after said first and second plates are mounted on said plurality of interfitting joints;
 wherein said plurality of interfitting joints permitting sliding movement of each of said first plate and said second plate on said housing.

* * * * *